(12) United States Patent
Stansbury et al.

(10) Patent No.: US 11,597,735 B2
(45) Date of Patent: Mar. 7, 2023

(54) HIGHLY EFFICIENT FREE RADICAL PHOTOPOLYMERIZATIONS THROUGH ENABLED DARK CURE

(71) Applicant: THE REGENTS OF THE UNIVERSITY OF COLORADO, Boulder, CO (US)

(72) Inventors: Jeffrey W. Stansbury, Boulder, CO (US); Kangmin Kim, Boulder, CO (US); Charles B. Musgrave, Boulder, CO (US); Jasmine Sinha, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 251 days.

(21) Appl. No.: 16/770,725

(22) PCT Filed: Dec. 10, 2018

(86) PCT No.: PCT/US2018/064801
§ 371 (c)(1),
(2) Date: Jun. 8, 2020

(87) PCT Pub. No.: WO2019/113602
PCT Pub. Date: Jun. 13, 2019

(65) Prior Publication Data
US 2021/0163508 A1 Jun. 3, 2021

Related U.S. Application Data

(60) Provisional application No. 62/596,185, filed on Dec. 8, 2017.

(51) Int. Cl.
| | | |
|---|---|---|
| *C08F 2/50* | (2006.01) | |
| *C07D 311/16* | (2006.01) | |
| *C07D 311/56* | (2006.01) | |
| *C07D 311/92* | (2006.01) | |
| *G03F 7/029* | (2006.01) | |
| *C07F 5/02* | (2006.01) | |
| *G03F 7/004* | (2006.01) | |

(52) U.S. Cl.
CPC ............ *C07F 5/027* (2013.01); *C07D 311/16* (2013.01); *C07D 311/56* (2013.01); *C07D 311/92* (2013.01); *C08F 2/50* (2013.01); *G03F 7/0045* (2013.01); *G03F 7/029* (2013.01)

(58) Field of Classification Search
CPC ..... C07F 5/027; C07D 311/16; C07D 311/56; C07D 311/92; C08F 2/50; G03F 7/0045; G03F 7/029
See application file for complete search history.

(56) References Cited

U.S. PATENT DOCUMENTS

| | | |
|---|---|---|
| 5,952,152 A | 9/1999 | Cunningham et al. |
| 6,096,794 A | 8/2000 | Cunningham et al. |
| 8,883,948 B2 | 11/2014 | Stansbury et al. |
| 2006/0269873 A1 | 11/2006 | Knight et al. |

OTHER PUBLICATIONS

Sarker et al., (10) J. of the Chem. Soc., Perkins Trans. 2: Physical Org. Chem. 2315-2322 (1998) (Year: 1998).*
Aguirre-Soto, et al., "Visible-Light Organic Photocatalysis for Latent Radical-Initiated Polymerization via 2e-/1H+ Transfers: Initiation with Parallels to Photosynthesis" Journal Of The American Chemical Society (2014), vol. 136, 7418-7427.
Denney, et al., "Studies of the Mechanisms of the Reaction of Benzoyl Peroxide with Secondary Amines and Phenols" Journal of American Chemical Society vol. 136(20) pp. 7412-7427 (2014).
He, et al., "N-Phthaloyltranexamic acid ammonium salt derivatives as photocaged superbase for redox free radical photopolymerization" Polymer Chemistry (2014) vol. 5, 2951-2960.
He, et al., "Photoinduced redox initiation for fast polymerization of acrylaytes based on latent superbase and peroxides" Polymer vol. 53 (2012) 3172-3177.
International Search Report dated Mar. 28, 2019; International Application No. PCT/US2018/064801; International Filing Date Dec. 10, 2018 (4 pgs).
Written Opinion dated Mar. 28, 2019; International Application No. PCT/US2018/064801; International Filing Date Dec. 10, 2018 (5 pgs).
Xu, et al., "Benzoylformamides as versatile photocaged bases for redox free radical photopolymerization" Photochem. Photobio. Sci., 2016, vol. 15, 1442-1447.

* cited by examiner

*Primary Examiner* — Timothy R Rozof
(74) *Attorney, Agent, or Firm* — Cantor Colburn LLP

(57) ABSTRACT

A quaternary ammonium salt comprising a chromophore constituent, a tertiary amine cation constituent connected to the para-position of the chromophore constituent via a methylene linkage, and a borate anion constituent, wherein chromophore constituent is a 3-ketocoumarin constituent or a benzophenone constituent. Also, a photobase-redox initiating system comprising the quaternary ammonium salt and a peroxide.

11 Claims, 20 Drawing Sheets

Type A
QA-DBU-TPB

Type B
Phthal-DBU

Type C

TBB NBB

Figure 29

| | | | |
|---|---|---|---|
| Structure | [benzophenone structure] | [dimethoxy-KC structure] | [di-n-butoxy-KC structure] |
| Name | Benzophenone | dimethoxy-KC | di-n-butoxy-KC |
| LUMO (Hartree) | -0.15266 | -0.14311 | -0.14162 |
| Absorption | Violet | Green | Green |
| PBG₄ HOMO (Hartree) | -0.12367 | -0.13664 | -0.13821 |

| | | | |
|---|---|---|---|
| Structure | [difluoro-KC structure] | [diphenyl-KC structure] | [divinyl-KC structure] |
| Name | difluoro-KC | diphenyl-KC | divinyl-KC |
| LUMO (Hartree) | -0.14865 | -0.14228 | -0.14299 |
| Absorption | Green | Yellow | Yellow |
| PBG₄ HOMO (Hartree) | -0.13857 | -0.13340 | -0.13328 |

| | | |
|---|---|---|
| Structure | [trimethoxy-KC structure] | [tetramethoxy-KC structure] |
| Name | trimethoxy-KC | tetramethoxy-KC |
| LUMO (Hartree) | -0.14220 | -0.14627 |
| Absorption | Blue | Green |
| PBG₄ HOMO (Hartree) | -0.13531 | -0.14592 |

Figure 30
| Structure | 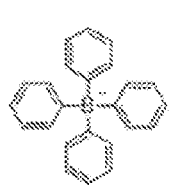 | 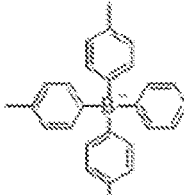 | 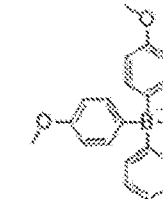 | 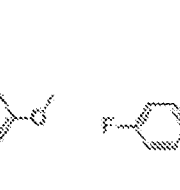 |
|---|---|---|---|---|
| Name | tetraphenyl | tetra-4-methyl-phenyl | tetra-4-methoxy-phenyl | tetra-4-fluoro-phenyl |
| HOMO (Hartree) | -0.19904 | -0.18904 | -0.18812 | -0.21762 |
| Structure | 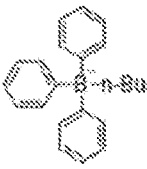 | 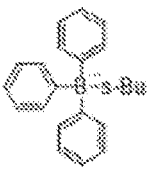 | 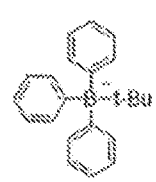 | 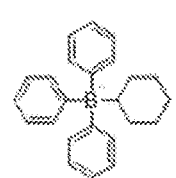 |
|---|---|---|---|---|
| Name | n-butyl-triphenyl | s-butyl-triphenyl | t-butyl-triphenyl | cyclohexyl-triphenyl |
| HOMO (Hartree) | -0.19105 | -0.18948 | -0.18706 | -0.19101 |
| Structure | 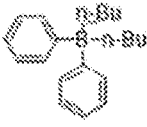 | 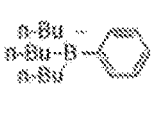 | 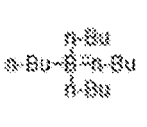 |
|---|---|---|---|
| Name | di-n-butyl-diphenyl | tri-n-butyl-phenyl | tetra-n-butyl |
| HOMO (Hartree) | -0.18035 | -0.16964 | -0.16388 |

Figure 31

| Structure | (N-methyl morpholine) | (N-methyl pyrrolidine) | (N,N-dimethyl aniline) | (N,N,4-trimethyl aniline) |
|---|---|---|---|---|
| Name | N-methyl morpholine | N-methyl pyrrolidine | N,N-dimethyl aniline | N,N,4-trimethyl aniline |
| Exp. Polym. Rate ($\mu mol\ s^{-1}$) | 0.9 ± 0.2 | 2.3 ± 0.4 | 3.1 ± 0.2 | 5.3 ± 0.9 |
| Comp. Redox Rates ($s^{-1}$) | $2.0 \times 10^{-10}$ | $3.1 \times 10^{-8}$ | $3.6 \times 10^{-6}$ | $3.3 \times 10^{-5}$ |
| pKa (aq) | 7.4 | 10.3 | 5.1 | 5.6 |

| Structure | | | |
|---|---|---|---|
| Name | N,N-dimethyl -4-methoxyaniline | N,N-pyrrolidine -4-methoxyaniline | N,N-ethoxy -4-methylaniline |
| Exp. Polym. Rate ($\mu mol\ s^{-1}$) | 12.3 ± 1.0 | Too rapid to measure | Due to high steric reactive nitrogen, long induction time is achieved through slow $S_N 2$ without compromising latent radical generation. |
| Comp. Redox Rates ($s^{-1}$) | $4.5 \times 10^{-4}$ | $1.9 \times 10^{-2}$ | |

Figure 32

| Name | Benzoyl peroxide 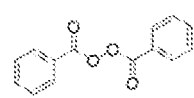 | dilauroyl peroxide 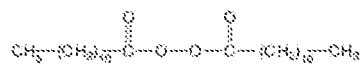 |
|---|---|---|
| *Comp. Redox Rates (s⁻¹)* | $1.3 \times 10^{-11}$ | $4.3 \times 10^{-12}$ |
| Redox Reactivity | Moderate | Moderate |
| Thermal Stability | Stable below 80*C | Stable below 50*C |

| Name | Dialkylperoxy dicarbonate | Phthaloyl Peroxide | Dicumyl peroxide |
|---|---|---|---|
| *Comp. Redox Rates (s⁻¹)* | $1.7 \times 10^{-9}$ | $9.4 \times 10^{-6}$ | $1.9 \times 10^{-22}$ |
| Redox Reactivity | Moderate | Fast | Very slow |
| Thermal Stability | Stable below 5*C | Stable below 90*C | Stable below 75*C |

HIGHLY EFFICIENT FREE RADICAL PHOTOPOLYMERIZATIONS THROUGH ENABLED DARK CURE

CROSS-REFERENCE TO RELATED APPLICATIONS

This application is a National Stage application of PCT/US2018/064801, filed Dec. 10, 2018, which claims the benefit of U.S. Provisional Application No. 62/596,185, filed Dec. 8, 2017, both of which are incorporated by reference herein in their entirety.

STATEMENT REGARDING FEDERALLY SPONSORED RESEARCH OR DEVELOPMENT

This invention was made with government support under R01DE023197 awarded by NIH/NIDCR. The government has certain rights in the invention.

FIELD OF THE INVENTION

UV and visible photo-base-generators that can release a range of reactivity-tailored redox-active amines as well as generate direct free radical production to achieve both immediate and latent polymerization during and beyond the photo-activation stimulus. These generators are useful for photo-activated dark curing in photopolymerization as well as other applications.

BACKGROUND OF INVENTION

Radical polymerization represents the most widely investigated and utilized approach for polymer synthesis with 40-45% of the ~350 million metric tons of annual worldwide industrial polymer production based on this chemistry due to their facile and flexible reaction conditions, compatibility with solvents and water, as well as their wide tolerance for a tremendous variety of functional comonomers. Specifically, light-initiated radical photopolymerization (RPP) is widely recognized and rapidly growing as an important green technology relative to conventional thermal polymerization because of its potential to reduce energy consumption and waste, while increasing productivity. In contrast to thermal polymerization, photopolymerization brings the advantages of ambient temperature processing, with fewer side reactions, and well-controlled onset and rate of polymerization based on the light source and photocuring conditions employed.

The spatial and temporal controls afforded by on-demand light initiation are highly desirable in photolithography and 3-D printing yet restrict the broad use of RPP in a multitude of polymeric material applications. In conventional free radical photoinitiated polymerizations, initiation, propagation and termination occur simultaneously during light exposure. When irradiance ends, radical production stops and propagation quickly drops to near zero due to efficient bi-radical termination. Trapped radicals can persist in the high-conversion, vitrified state but the restricted network mobility excludes access of radicals to regions of lower conversion, which limits significant post-cure. This means that irradiance during free radical photopolymerization must extend until the least light-accessible region of the sample has achieved full conversion. Any low conversion regions within an undercured polymer contribute to compromised properties that cannot be rectified without additional irradiation. In flat, optically thin films, sufficient light exposure is not a significant problem; however, when irregular surfaces that offer a wide range of incident irradiance levels or when thick layers and/or filled materials that present significant light attenuation are considered for photocuring processes, the well-recognized efficiency of photopolymerization can be greatly reduced.

Methylene blue (MB+) has been used as photo-sensitizer with a hindered amine reductant and diphenyl iodonium salt (DPI) oxidant. Aguirre-Soto et al., *Visible-Light Organic Photocatalysis for Latent Radical-Initiated Polymerization via 2e(−)/1H(+) Transfers: Initiation with Parallels to Photosynthesis,* Journal of the American Chemical Society, vol. 136 (20), pp 7418-7427 (2014); Stansbury, Methods for extensive dark curing based on visible-light initiated, controlled radical polymerization; U.S. Pat. No. 8,883,948. This photoinitiator undergoes a two-electron/one-proton transfer with the amine to give a neutral, meta-stable leuco-methylene blue (LMB) without radical production and no direct polymerization associated with the photo-activation step. In a second, slower reaction, LMB undergoes a redox reaction with DPI to reform MB+ while producing two initiating phenyl radicals. It was demonstrated that photo-bleaching of MB+ with latent redox-based radical production lasted for hours to yield fully converted polymer with much or even complete conversion occurring in the dark phase. This approach was effective but was restricted by pre-cure instability and a number of other practical limitations including the slow onset of polymerization.

A photo-activated amine/peroxide redox polymerization was used to demonstrate dark curing in solvated acrylic resins. He et al., *Photoinduced redox initiation for fast polymerization of acrylates based on latent superbase and peroxides,* Polymer, vol 53 (15), pp 3172-3177 (2012); He et al., *N-Phthaloyltranexamic acid ammonium salt derivatives as photocaged superbase for redox free radical photopolymerization,* Polymer Chemistry, vol. 5 (8), pp 2951-2960 (2014). The photoinitiators were benzophenone-based ammonium salt with tetraphenylborate (TPB) and N-phthaloyltranexamic acid ammonium salt, both of which release 1,8-diazabicylco[5.4.0]unde-7-ene (DBU) as a result of UV irradiation (QA-DBU-TPB and Phthal-DBU, respectively). DBU is routinely used as a highly basic amine (pKa(aq)= 13.5) in organic chemistry. The photo-released DBU amine reacted with benzoyl peroxide (BPO) homogenously present in the resin. The photopolymerization protocol included a formulation of 0.2-0.3 mmol of photoinitiators and BPO in 0.5 mL acetone or dimethyl sulfoxide (DMSO) and 0.9 mL trimehylolpropane triacrylate (TMPTA) where the role of solvent was to solubilize an ionic complex of highly nitrogenous compounds with numerous phenyl rings in low-polarity multi-acrylate resins. The chemical structures of this system are shown in FIG. 1. The disclosed dark cure inititiating techniques, however, do not work in bulk resin systems.

SUMMARY OF INVENTION

In one embodiment the invention is directed to a quaternary ammonium salt comprising a chromophore constituent, a tertiary amine cation constituent connected to the para-position of the chromophore constituent via a methylene linkage, and a borate anion constituent, wherein chromophore constituent is a 3-ketocoumarin constituent and the quaternary ammonium salt has the formula (I) or the chromophore constituent is a benzophenone constituent and the quaternary ammonium salt has the formula (II)

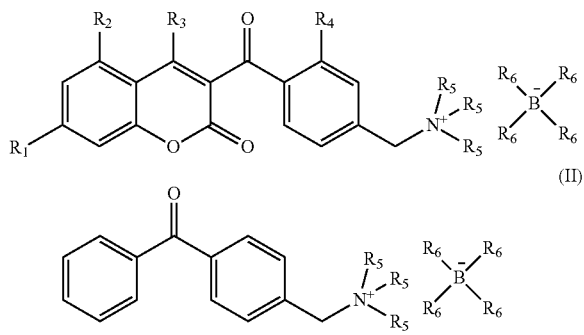

wherein:
R$_1$ and R$_2$, identical or different, are independently selected from the group consisting of —H, —OH, linear or branched C$_1$-C$_8$-alkoxy group,

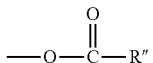

where R" is a linear or branched C$_1$-C$_8$ alkyl group, unsubstituted or substituted -phenyl group, unsubstituted or substituted -napthyl group, unsubstituted or substituted -vinyl group, -halogen, and halogenated C$_1$-C$_8$-alkyl group;

R$_3$ is selected from the group consisting of independently selected from the group consisting of —H, —OH, linear or branched C$_1$-C$_8$-alkoxy group, -halogen, and halogenated -alkyl group;

R$_4$ is selected from the group consisting of independently selected from the group consisting of —H, —OH, linear or branched C$_1$-C$_8$-alkoxy group, -halogen, and halogenated C$_1$-C$_8$-alkyl group;

R$_5$, identical or different, is independently selected from the group consisting of linear or branched C$_1$-C$_8$ N-alkyl group; hydroxyl-substituted C$_1$-C$_8$ N-alkyl group; fused 5-7 member heterocyclic ring; and unsubstituted or substituted aromatic ring, wherein the substituent on the aromatic ring is selected from the group consisting of linear or branched C$_1$-C$_8$ alkyl group and linear or branched C$_1$-C$_8$ alkoxy group; and R$_6$, identical or different, is independently selected from the group consisting of linear or branched C$_1$-C$_8$ alkyl group, and unsubstituted or substituted aromatic ring wherein the substituent on the aromatic ring is selected from the group consisting of linear or branched C$_1$-C$_8$ alkyl group, linear or branched C$_1$-C$_8$ alkoxy group, and halogen.

In another embodiment, the invention is directed to a photobase-redox initiating system comprising said quaternary ammonium salt and a peroxide selected from the group consisting of benzoyl peroxide, dilauroyl peroxide, dialkylperoxydicarbonate, phtaloyl peroxide, dicumyl peroxide, and combinations thereof.

BRIEF DESCRIPTION OF THE DRAWINGS

FIG. 29 show exemplary chromophores with the associated computationally derived photochemical properties.

FIG. 30 shows exemplary borates with the calculated HOMO levels.

FIG. 31 shows exemplary amines that are active in amine-peroxide redox polymerization with reaction rates and pKa.

FIG. 32 shows exemplary peroxides with various computational redox reactivities and thermal stability.

DETAILED DESCRIPTION OF INVENTION

Terminology

Figure 1:
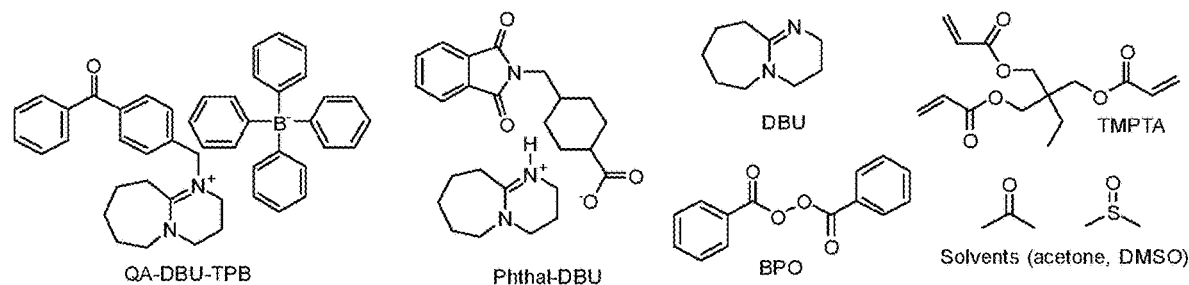
FIG. 1 shows the chemical structures of photoinitiators QA-DBU-TPB and Phthal-DBU, photo-released amine (DBU), peroxide oxidant (BPO), trifunctional acrylate (TMPTA), and solvating solvents acetone and DMSO.

As used herein, the following definitions shall apply unless otherwise indicated.

"Visible light" refers to light having a wavelength of about 400 to 1000 nanometers (nm).

"Initiation" refers to subjecting the composition to a visible-light source for a given period of time.

"Radical polymerization" refers to polymerization in which the reactive center of the polymer chain is a radical.

"Dark curing" refers to continued polymerization after the visible light source has been removed, i.e., the radical active center is not immediately terminated when the visible-light source is removed.

"Optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that (contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to twelve carbon atoms.

The terms "alkenyl" and "alkynyl" used alone or as part of a larger moiety shall include both straight and branched chains containing two to twelve carbon atoms.

The term "halogen" or "halo" means F, Cl, Br or I.

The terms "haloalkyl," "haloalkenyl, and "haloalkoxy" or "halogenated" with respect alkyl, alkenyl or alkoxy means alkyl, alkenyl or alkoxy, respectively, substituted with one or more halogen atoms.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring".

The term "aralkyl" refers to an alkyl group substituted by an aryl. The term "aralkoxy" refers to an alkoxy group substituted by an aryl.

The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl. An aryl (including aralkyl, aralkoxy, aryloxyalkyl and the like) or heteroaryl (including heteroaralkyl, heteroarylalkoxy and the like) group may contain one or more substituents. Suitable substituents on an unsaturated carbon atom of an aryl, heteroaryl, aralkyl or heteroaralkyl group are selected from halogen; haloalkyl; —CF$_3$; —R; —OR; —SR; 1,2-methylenedioxy; 1,2-ethylenedioxy; protected OH (such as acyloxy); phenyl (Ph); Ph substituted with R; —O(Ph); —O-(Ph) substituted with R; CH$_2$(Ph); —CH$_2$(Ph) substituted with R; —CH$_2$CH$_2$(Ph); —CH$_2$CH$_2$(Ph) substituted with R; —NO$_2$; —CN; —N(R)$_2$; —NRC(O)R; —NRC(O)N(R)$_2$; —NRCO$_2$R; —NRNRC(O)R; —NR—NRC(O)N(R)$_2$; —NRNRCO$_2$R; —C(O)C(O)R; —C(O)CH$_2$C(O)R; —CO$_{2R}$; —C(O)R; —C(O)N(R)$_2$; —OC(O)N(R)$_2$; —S(O)$_2$R; —SO$_2$N(R)$_2$; —S(O)R; —NRSO$_2$N(R)$_2$; —NRSO$_2$R; —C(=S)N(R)$_2$; —C(=NH)—N(R)$_2$; —(CH$_2$)J, NHC(O)R; —(CH$_2$)J, R; —(CH$_2$)J, NHC(O)NHR; —(CH$_2$)J, NHC(O)OR; —(CH$_2$)$_y$, NHS(O)R; —(CH$_2$)$_y$, NHSO$_2$R; or —(CH$_2$)J, NHCO)CH((V)z-R)(R) wherein each R is independently selected from hydrogen, optionally substituted C$_{1-6}$ aliphatic, an unsubstituted 5-6 membered heteroaryl or heterocyclic ring, phenyl (Ph), —O(Ph), or —CH$_2$(Ph)—CH$_2$(Ph), wherein y is 0-6; z is 0-1; and V is a linker group. When R is C$_{1-6}$ aliphatic, it may be substituted with one or more substituents selected from —NH$_2$, —NH(C$_{1-4}$aliphatic), —N(C$_{1-4}$ aliphatic)$_2$—S(O)(C$_{1-4}$ aliphatic), —SO$_2$ (C$_{1-4}$ aliphatic), halogen, (C$_{1-4}$ aliphatic), —OH, —O—(C$_{1-4}$ aliphatic), —NO$_2$, —CN, —CO$_2$H, CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

An aliphatic group or a non-aromatic heterocyclic ring may contain one or more substituents. Suitable substituents on a saturated carbon of an aliphatic group or of a nonaromatic heterocyclic ring are selected from those listed above for the unsaturated carbon of an aryl or heteroaryl group and the following: =O, =S, =NNHR, =NN(R)$_2$, =N—, =NNHC(O)R, =NNHCO$_2$(alkyl), =NNHSO$_2$(alkyl), or =NR, where each R is independently selected from hydrogen or an optionally substituted C$_{1-4}$ aliphatic. When R is C$_{1-4}$aliphatic, it may be substituted with one or more substituents selected from —NH$_2$, —NH(C$_{1-4}$aliphatic), —N(C$_{1-4}$ aliphatic)$_2$, halogen, —OH, —O—(C$_{1-4}$aliphatic), —NO$_2$, —CN, —CO$_2$H, —CO$_2$(C$_{1-4}$aliphatic), —O(halo C$_{1-4}$aliphatic), or -halo(C$_{1-4}$aliphatic); wherein each C$_{1-4}$ aliphatic is unsubstituted.

A vinyl, or "vinylene," functional group suitable for embodiments of the present invention includes any monomer having one or more vinyl functional groups, i.e., reacting "—C=C—" groups. Synonyms for a vinyl functional group include the terms olefinic group, alkenyl group, and ethylenic group.

In one embodiment the invention is directed to a quaternary ammonium salt comprising a chromophore constituent, a tertiary amine cation constituent connected to the para-position of the chromophore constituent via a methylene linkage, and a borate anion constituent, wherein chromophore constituent is a 3-ketocoumarin constituent and the quateranary ammonium salt has the formula (I) or the chromophore constituent is a benzophenone constituent and the quateranary ammonium salt has the formula (II)

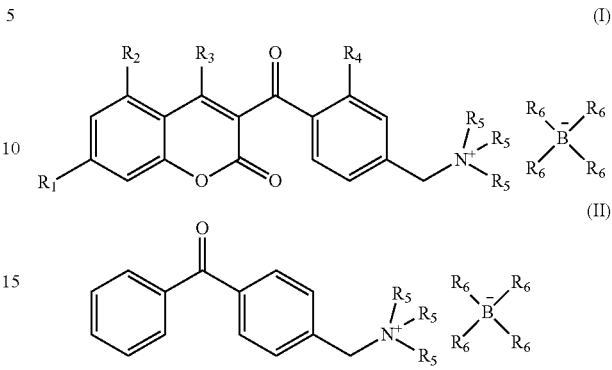

wherein:

R$_1$ and R2, identical or different, are independently selected from the group consisting of —H, —OH, linear or branched C$_1$-C$_8$-alkoxy group,

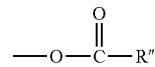

where R" is a linear or branched C$_1$-C$_8$ alkyl group, unsubstituted or substituted -phenyl group, unsubstituted or substituted -napthyl group, unsubstituted or substituted -vinyl group, -halogen, and halogenated C$_1$-C$_8$-alkyl group;

R$_3$ is selected from the group consisting of independently selected from the group consisting of —H, —OH, linear or branched C$_1$-C$_8$-alkoxy group, -halogen, and halogenated -alkyl group;

R$_4$ is selected from the group consisting of independently selected from the group consisting of —H, —OH, linear or branched C$_1$-C$_8$-alkoxy group, -halogen, and halogenated C$_1$-C$_8$-alkyl group;

R$_5$, identical or different, is independently selected from the group consisting of linear or branched C$_1$-C$_8$ N-alkyl group; hydroxyl-substituted C$_1$-C$_8$ N-alkyl group; fused 5-7 member heterocyclic ring; and unsubstituted or substituted aromatic ring, wherein the substituent on the aromatic ring is selected from the group consisting of linear or branched C$_1$-C$_8$ alkyl group and linear or branched C$_1$-C$_8$ alkoxy group; and R$_6$, identical or different, is independently selected from the group consisting of linear or branched C$_1$-C$_8$ alkyl group, and unsubstituted or substituted aromatic ring wherein the substituent on the aromatic ring is selected from the group consisting of linear or branched C$_1$-C$_8$ alkyl group, linear or branched C$_1$-C$_8$ alkoxy group, and halogen.

Alkoxy Groups

In certain embodiments, each alkoxy group is independently selected from the group consisting of methoxy and butoxy.

3-ketocoumarin Constituent Chromophore

$R_1$ and $R_2$

Phenyl Group

In certain embodiment, the substituted -phenyl group has one or more independently selected substituents selected from the group consisting of linear or branched $C_1$-$C_8$ alkyl group, linear or branched $C_1$-$C_8$-alkoxy group, -halogen, and halogenated $C_1$-$C_6$-alkyl group.

Napthyl Group

In certain embodiment, the substituted napthyl group has one or more independently selected substituents selected from the group consisting of linear or branched $C_1$-$C_8$ alkyl group, linear or branched $C_1$-$C_8$-alkoxy group, -halogen, and halogenated $C_1$-$C_6$-alkyl group.

Vinyl Group

In certain embodiments, the unsubstituted vinyl group is $C_2$ and the substituted vinyl group is an extended vinylene up to $C_{10}$.

$R_3$ $R_3$ differs from $R_1$ and $R_2$ based on accessibility to the radical produced on homolysis as well as the undesired potential to react with that radical. So, in certain embodiments $R_3$ is selected from the group consisting of —H, -halogen, and alkoxy (in certain embodiments butoxy or methoxy).

In one embodiment, $R_3$ is —H or alkoxy.
In one embodiment, $R_3$ is —H.
In certain embodiments, $R_3$ is -halogen. In one such embodiment, $R_3$ is —F.

In one embodiment, the chromophore constituent is the 3-ketocoumarin constituent, which is selected from the group consisting of 3-ketocoumarin chromophore constituent is dimethoxy-ketocoumarin, di-n-butoxy-ketocoumarin, difluoro-ketocoumarin, diphenyl-ketocoumarin, divinyl-ketocoumarin, trimethoxy-ketocoumarin, tetramethoxy-ketocoumarin, 3,4-benzo-ketocoumarin, and 4,5-benzo-ketocoumarin

Amine Cation $R_5$ does not include any —H groups.
In certain embodiments, at least one of the $R_5$ groups is the substituted aromatic ring.
In one embodiment, the amine cation constituent is selected from the group consisting of N-methyl morpholine, N-methyl pyrrolidine, N,N-dimethyl aniline, N,N,4-trimethyl aniline, N-N-dimethyl-4-methoxyaniline, N,N-pyrrolidine-4-methoxyaniline, and N,N-ethoxy-4-methylaniline.

Borate Anion

In one embodiment, the borate anion constituent is selected from the group consisting of tetraphenyl, tetra-4-methyl-phenyl, tetra-4-methoxy-phenyl, tetra-4-fluoro-phenyl, n-butyl-triphenyl, s-butyl-triphenyl, t-butyl-triphenyl, cyclohexyl-triphenyl, di-n-butyl-diphenyl, tri-n-butyl-phenyl, and tetra-n-butyl.

For the borate anion, the substitution of alkyl groups for aromatic rings enhances the solubility of the initiator in nonpolar monomer.

Photobase-redox Initiating System

In one embodiment, the invention is directed to a photobase-redox initiating system comprising the quaternary ammonium salt as described above and a peroxide selected from the group consisting of benzoyl peroxide, dilauroyl peroxide, dialkylperoxydicarbonate, phtaloyl peroxide, dicumyl peroxide, and combinations thereof.

The approach detailed here involves a photo-base-generator that liberates an amine that then participates in a free radically initiated redox polymerization process with a peroxide or other oxidant, which can proceed for minutes to hours after a brief initial light exposure. Notably, initiating radicals are efficiently produced during the photolysis process, which enables rapid, direct photopolymerization in addition to the redox radical generation that does not require continued irradiation.

This disclosure covers the development of UV and visible photo-base-generators that can release a range of reactivity-tailored redox-active amines as well as generate direct free radical production to achieve both immediate and latent polymerization during and beyond the photo-activation stimulus. This system is useful for photo-activated dark curing in photopolymerization as well as other applications.

We have demonstrated a single-part, photo-initiated formulation with near-UV wavelength (365 nm) that displays good shelf-life stability in (meth)acrylic resins and rapid photocuring where sufficient light access is available while inducing extended "dark-cure" radical production and effective polymer post-cure without additional irradiation within the regions that received even very limited exposure.

We also have demonstrated the advanced understanding of the responsible redox initiation mechanism behind the dark-curing phenomena and the ability to suggest various amines and peroxides with different dark curing abilities as well as eliminate others that show minimal initiating activity for dark curing.

We additionally have developed visible light photo-base generators that can absorb visible-wavelength light and demonstrated similar convincing evidence of dark curing induced by 400-455 nm LEDs. Such conclusive development will allow processing of thin films and thick bulk polymer to achieve full conversion with minimal light exposure in an extremely photon-efficient manner.

This work has application to coatings, adhesives, graphic arts, stereolithography, photoresists, laser direct imaging, computer-to-plate technology, holographic optical elements, micro-devices and dental/biomaterials.

This new technology will provide confidence in the complete through-cure and predictably maximized final polymer properties with limited irradiation despite resin thickness, pigments, fillers, or photocuring limitations. This also applies directly to all applications involving photobase generators for applications other than photopolymerization as well as use of amines and peroxide as redox pairs including but not limited to amine-peroxide redox polymerization Our group has worked to produce practical dark curing initiators using a similar motif of photo-releasable amines and latent redox polymerization. We demonstrate that we have dramatically improved dark curing efficiency, photopolymerization efficiency, solubility, and wavelength modulation to render this technology practical. A typical dark curing capability from our dark curing photoinitiators is displayed in FIG. 2 where no solvent was used to solvate the photoinitiators and more than 60% additional conversion is achieved through latent redox polymerization between the photo-released amine and BPO, highlighting our work of efficient and practical dark curing photoinitiator development.

EXAMPLES

Comparison Between Yang's Photoinitiators and Our Photoinitiators

Figure 3:
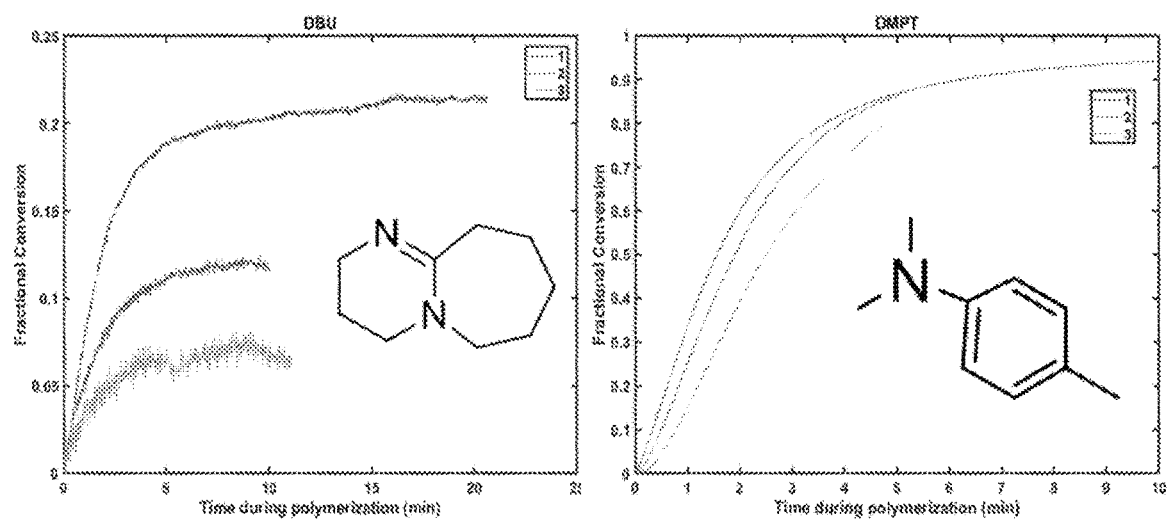
FIG. 3 is show FT-IR experimental polymerization kinetics with DBU and DMPT with BPO in monoacrylate without solvent at the same 3 mol % concentration.

We delineated the great differences in both direct photo-activated radical-initiating capability and in the redox-based dark-curing capability between the DBU amine (disclosed by the Yang group, see He et al.) and the N,N-dimethyl-p-toluidine amine, also known as DMPT. FIG. 3 demonstrates the redox-initiating capability of DBU and DMPT under identical conditions, where the amine and BPO concentrations are 3 mol % in monofunctional acrylate (di(ethylene glycol) ethyl ether acrylate). Even at the same concentrations, DBU barely achieved 20% conversion in 20 minutes while DMPT reached full conversion within 10 minutes.

Figure 4:
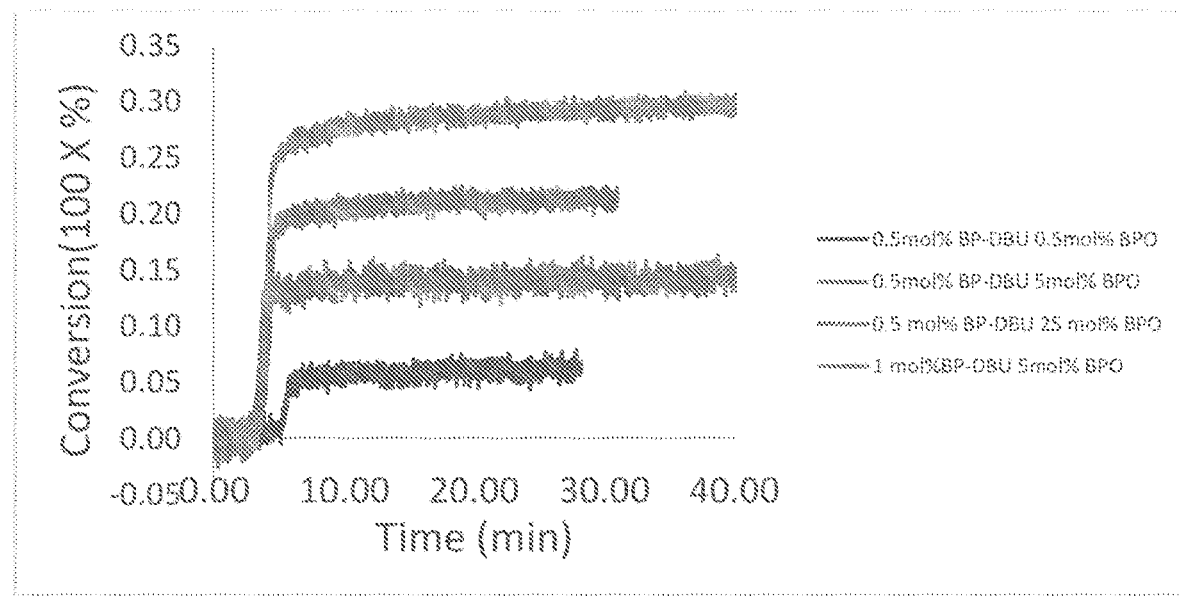
FIG. 4 demonstrates the dark curing capability of QA-DBU-TPB in analogous conditions as FIG. 2 in solvent-less neat resins.
Figure 5:
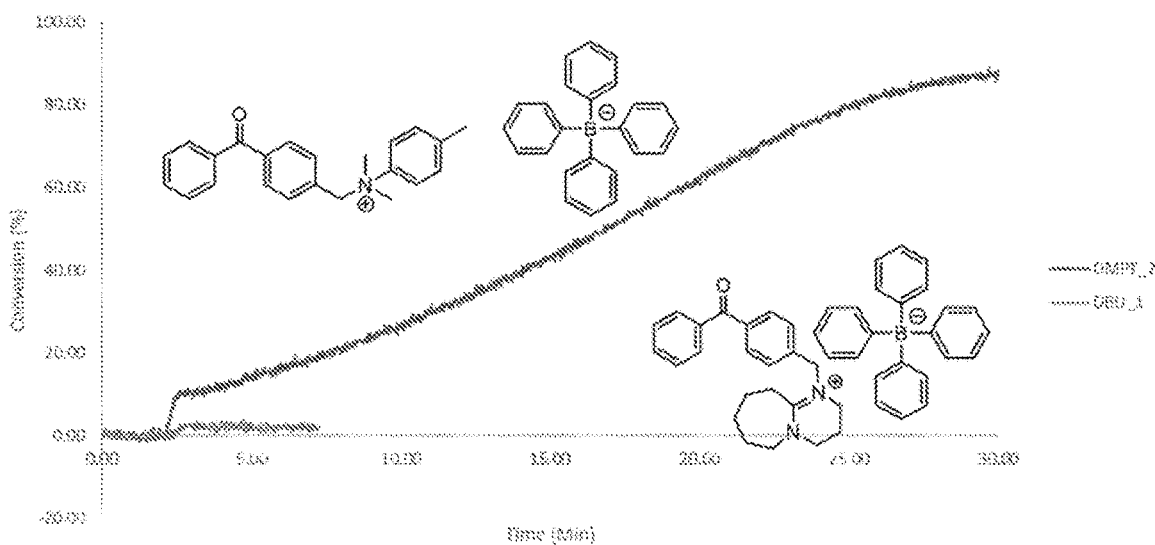
FIG. 5 is a comparison of the photopolymerization achieved under identical conditions and formulation, for a DMPT-based photoinitiator and the DBU-based photoinitiator.

Furthermore, we prepared the benzophenone-DBU photobase initiator described by the Yang group. This photoinitiator yielded low direct photopolymerization during light exposure and very limited dark cure when the light was extinguished at varied levels of partial cure (FIG. 4). We tried various concentration and conditions to test their photoinitiator, yet QA-DBU-TPB achieved only a small percentage of dark curing, indicating that DBU-based photoinitiators are impractical in polymerization without solvents. FIG. 5 demonstrates the stark difference between the photoinitiators disclosed by the Yang group and those disclosed herein under the same conditions, including the irradiation period. Primarily, this is because DBU has much higher activation barriers than DMPT for the amine-peroxide redox reaction. More particularly, FIG. 5 demonstrates the photoinitiator with DMPT photopolymerizes significantly better than the DBU-based photoinitiator due to the quantum yield difference by orders of magnitude. Despite structural similarity of chromophore, we were able to increase the quantum yield by understanding the mechanism. Namely, the generation of amine radical cation as an intermediate. Due to the high stability of DMPT radical cation vs. that of DBU, the former is more easily produced, and photo-radical generation is significantly more pronounced. Furthermore, DBU attacks comonomer (acrylonitrile) in a non-productive manner through Michael reaction compared to DMPT that promoted expanded radical polymerization in the dark. Stated another way, the nucleophilic nature of DBU limits the broad application of the DBU-based photoinitiator in resins that include strong Michael acceptor such as acrylonitrile, and some α,β-unsaturated ketones. The selection of DBU by the Yang group may have been due to a lack of understanding of the basic redox mechanism. While it may be effective in typical photobase applications where a strongly basic amine is desired, it has not been demonstrated as effective in redox chemistry applications. It is our belief that redox reactions are better facilitated by less basic amines with appropriate reduction potential.

Figure 6:
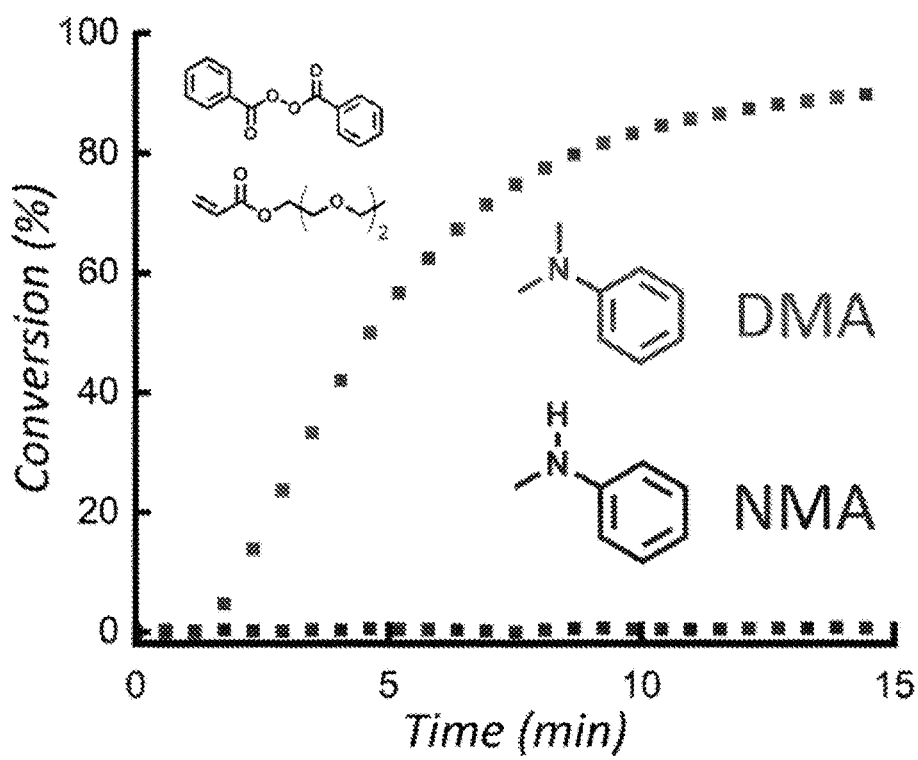
FIG. 6 shows FT-IR experimental polymerization kinetics with tertiary amine, DMA, and secondary amine, NMA, with BPO in monoacrylate without solvent at the same 3 mol % concentration.
Figure 7:
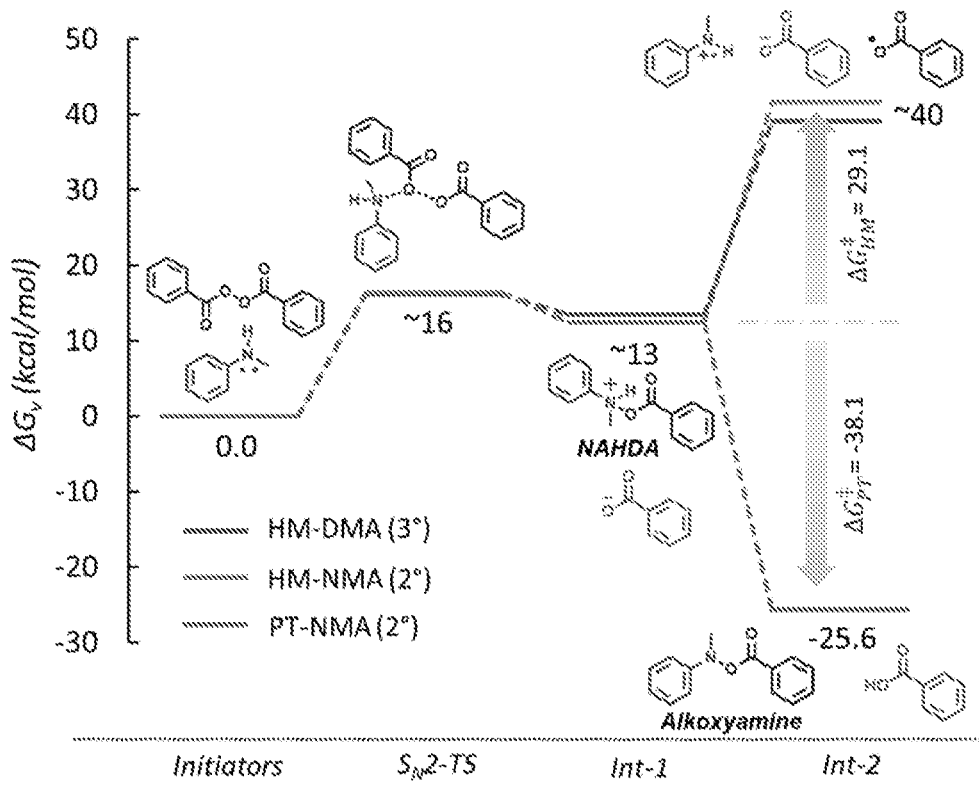
FIG. 7 shows the radical generating mechanism of tertiary amine (3°, blue), and the alternate mechanism of secondary amines (2°, green) that generates no radicals.

A separate concern raised with the reports provided by the Yang group is their claim of redox polymerization involving secondary amines and peroxides. Xu et al., *Benzolyformamides as versatile photocaged bases for redox free radical photopolymerization*, Photochemical & Photobiological Sciences vol 15 (11), pp 1442-1447 (2016). We demonstrated that secondary amines do not promote redox initiation through unreactive alkoxyamine production from our experimental and computational study reflected in FIGS. 6 and 7, respectively. Denney et al., *Studies of the Mechanisms of the Reactions of Benzoyl Peroxide with Secondary Amines and Phenols,* Journal of the American Chemical Society, vol 82, pp 1389-1393 (1960). In particular, FIG. 7 shows the homolysis (HM) pathways for N,N-dimethylaniline (DMA) and N-methyl aniline (NMA) share a similar energetics, showing a promise of initiating capability from NMA based on the previously discussed mechanism. However, an emerging proton transfer (PT) mechanism in N-acyloxyhydroxydialkylammonium (NAHDA), due to an acidic proton in the $N^+$—H bond, is more favorable than HM and yields a neutral alkoxyamine instead of radicals, rendering primary and 2° amines ineffective amine redox initiators. Hence most of the Yang photoinitiators do not exhibit dark curing and instead, along with their work exclusively in solvent and solvated monomer, require a prolonged irradiation for high conversion. In order to differentiate even further from their photoinitiators and maximize the potential for dark curing, we decided to study the amine peroxide redox reaction.

Dark Curing Efficiency

Figure 8:
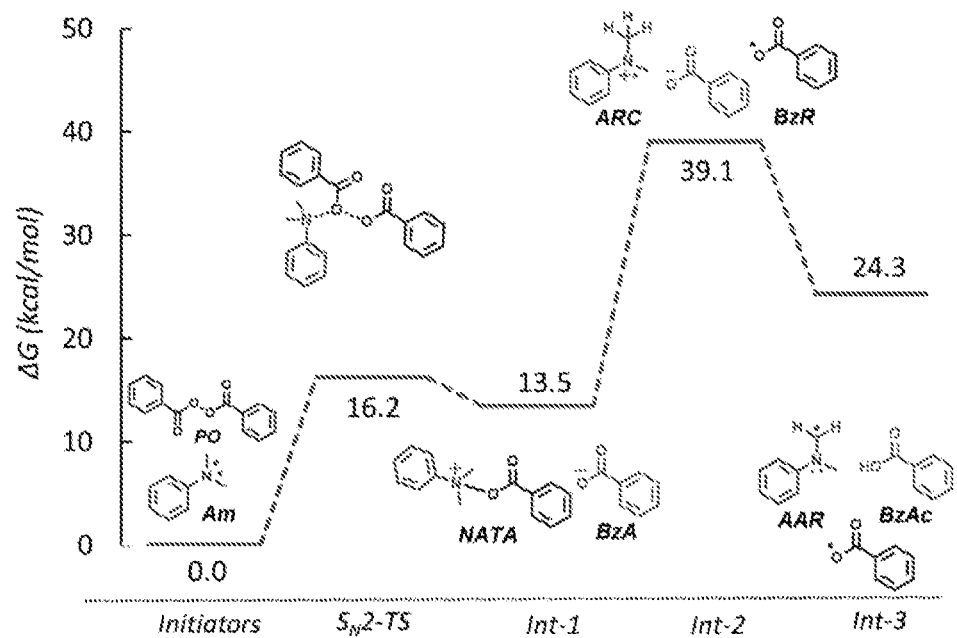
FIG. 8 shows the energetics of redox initiation between DMA and BPO.
Figure 9:
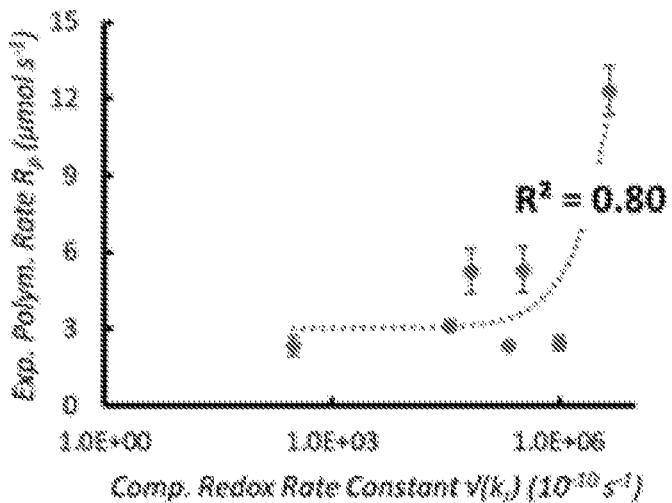
FIG. 9 shows a linear correlation between experimental polymerization rates (R$_p$) and the square root of the computed redox rate constants ($\sqrt{k_r}$) on a semi-log plot.

The dark curing efficiency (i.e., latent redox polymerization) originates from the redox reaction between liberated amine and peroxide. The combined approach of computational and experimental methods illuminate which amines and peroxides are suitable for dark curing usage. We studied the potential energy surface of amine-peroxide reaction between N,N-dimethylaniline (DMA) and BPO to elucidate the mechanism and identify potential rate-determining steps (FIG. 8). We found that $S_N2$ and homolysis steps have sufficiently high barriers to affect the radical generations and derived a kinetic equation that revealed the homolysis step is the true rate-determining step. With experimental kinetic studies, we confirmed that our proposed mechanism and derived kinetic equation sufficiently capture the redox-polymerization capability of various amines listed in Table 1 below as shown in FIG. 9. Referring to FIG. 9, the linear correlation between the experimental polymerization rates and the square root of the computed redox rate constants on a semi-log plot enables the reliable prediction of amine reactivities with BPO that can be used to guide the discovery of new amine reductants.

TABLE 1

Experimental and computational kinetic results for APRP

| | $^a$exp. Polym. Rate $R_p$ (µmol s$^{-1}$) | $^b$Comp. Rate Constant $(kr)^{1/2}$ (s$^{-1}$) |
|---|---|---|
| Amines with single active site conformation | | |
| PhPy | 2.4 ± 0.3 | 1.0 × 10$^{-4}$ |
| DMPT | 5.3 ± 0.9 | 3.3 × 10$^{-5}$ |
| MDMA | 12.3 ± 1.0 | 4.5 × 10$^{-4}$ |
| DMPEA | 2.3 ± 0.1 | 2.2 × 10$^{-5}$ |
| MePy | 2.3 ± 0.4 | 3.1 × 10$^{-8}$ |
| DMA | 3.1 ± 0.2 | 3.6 × 10$^{-6}$ |
| TeMA | 5.3 ± 0.9 | 6.8 × 10$^{-6}$ |
| Amines with multiple active site conformations | | |
| DEA | 0.3 ± 0.1$^c$ | 3.4 × 10$^{-4}$ |
| PhPi | 0.6 ± 0.2 | 6.9 × 10$^{-6}$ |
| MMP | 0.9 ± 0.2 | 2.0 × 10$^{-10}$ |

$^a$Based on average time of di(ethylene glycol) ethyl ether acrylate from 20% to 40% conversion to room temperature with 3 mol % amine and equivalent benzoyl peroxide to monomer, measured by FT-IR spectrophotometer
$^b$Based on Eyring equation computed with free energy (G,J from MN15/6-31 + G (d, p)/SMD-EtOAc.
$^c$Rate calculated from 10-20% conversion due to slow polymerization.

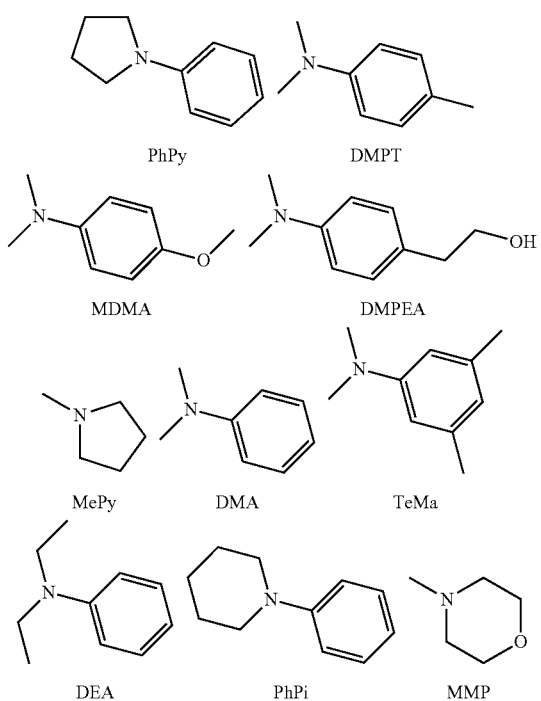

Figure 10:
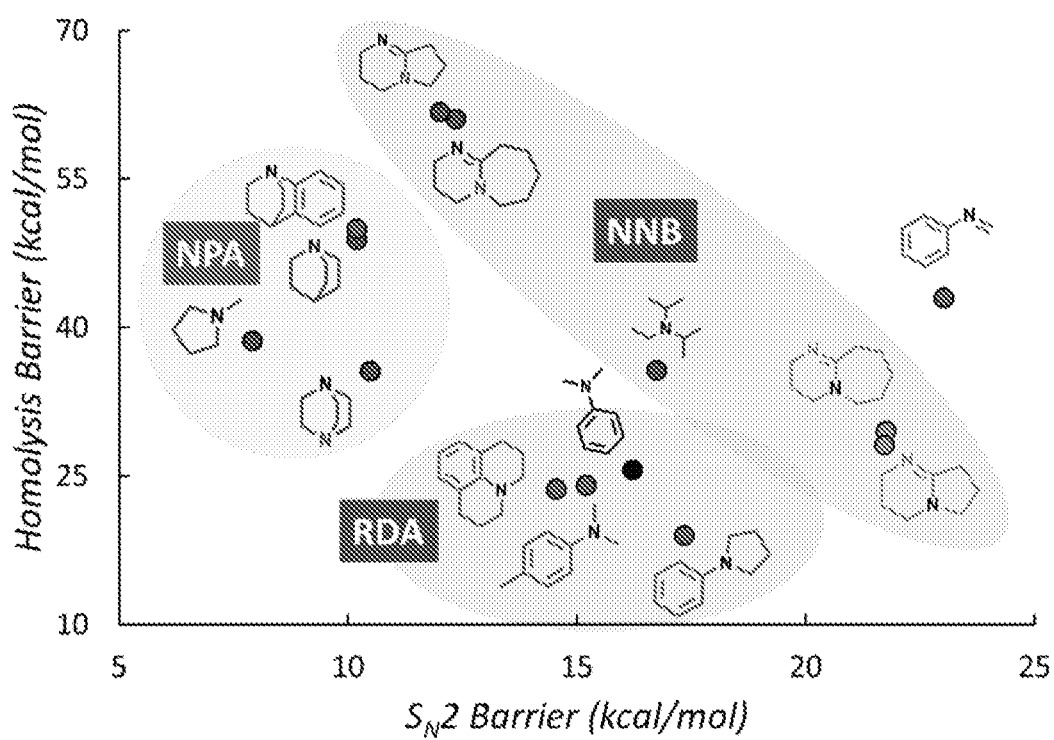
FIG. 10 are maps of the homolysis (HM) and S$_N$2 barriers from the following three amine categories: reducing amines (RDA), non-nucleophilic bases (NNB), and nucleophilic amines (NPA) with DMA shown for reference.

We then evaluated several classes of amines and found that aromatic amines outperformed other amines (FIG. 10). FIG. 10 displays a distinct relationship between the two barriers. The reducing aromatic amines (RDA in blue) perform the best in APRP as they have the lowest barriers for the rate-determining HM step, while amines with high basicity (NNB, non-nucleophilic bases in red) or nucleophilicity (NPA in green) are not promising for APRP due to high HM barriers. Aromatic amines that do not have optimal orbital orientations do not follow the trend of RDA and will not perform well for APRP, shown in purple. Two of the non-nucleophilic bases have two reactive sites that result in different energetics, marked by red and orange, separately. Reactive nitrogen is colored black.

Figure 11:
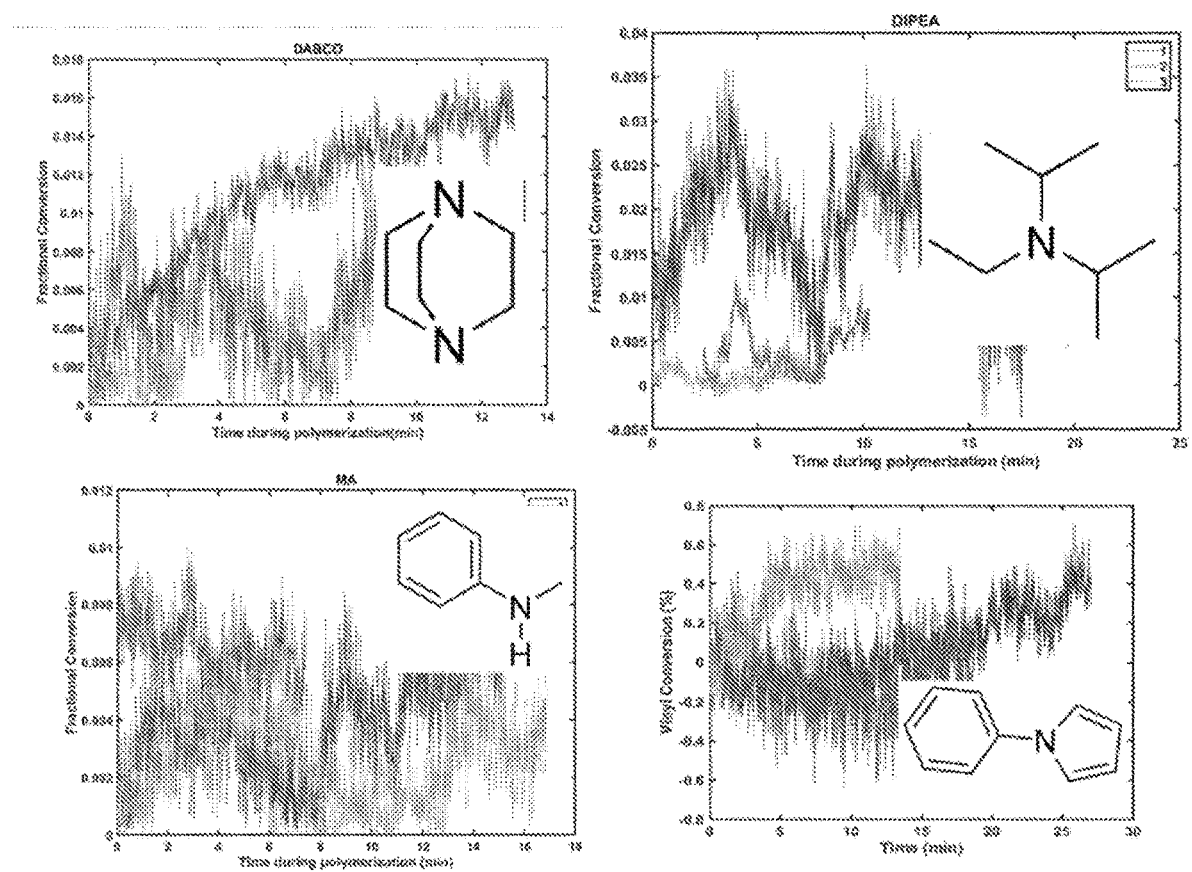
FIG. 11 show FT-IR experimental polymerization kinetics 1,4-Diazabicyclo[2,2,2]octane (DABCO), N,N-diisopropylethylamine (DIPEA), NMA, and 1-phenylpyrrole amines used with BPO in monoacrylate without solvent at the same 3 mol % concentration. These amines do not promote redox polymerization as they do not meet the requirements for being efficient reductants.
Figure 12:
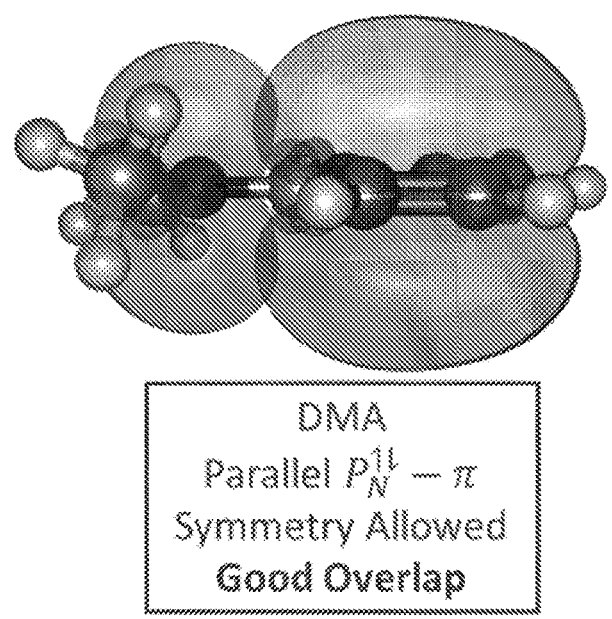
FIG. 12 is a depiction of the natural bond orbitals of the amine radical cations of N,N-dimethylaniline (DMA). The two orbitals shown are the P$_N^{1+}$ orbital and the π orbital of the phenyl rings. Note that the P$_N^{1+}$ and π orbitals of DMA spatially overlap to allow resonance that stabilizes the amine radical cation.
Figure 13:
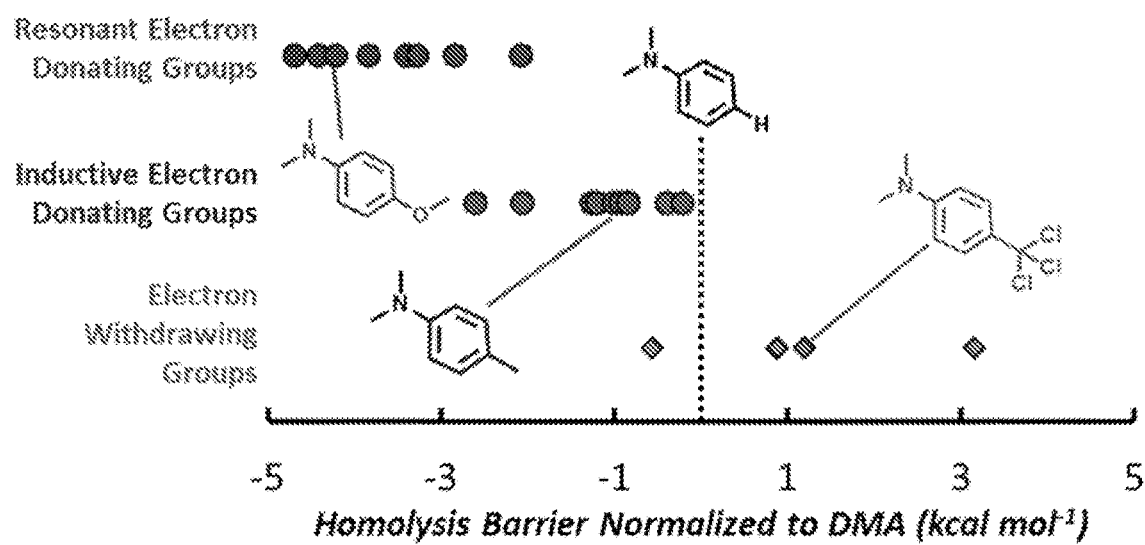
FIG. 13 shows homolysis (HM) barriers for para-substituted N,N-dimethyl aniline derivatives.

Experimental confirmation of FIG. 10 is shown in FIG. 11, where strong nucleophiles and bases as well as even the structurally similar amine to DMA can fail to promote redox polymerization if certain requirements are not met. For instance, aromatic amines can stabilize reaction intermediates more efficiently than others by orbital overlaps, and this can accelerate the redox reaction. (FIG. 12). This agreement between computational and experimental results further ensures that our prediction is in fact accurate. Furthermore, electron donating groups can stabilize reaction intermediates even further and will increase the redox initiating rates (FIG. 13). Specifically, FIG. 13 shows that substitutions with electron donating groups (EDG) resulted in lower HM barriers while those with electron withdrawing groups (purple) resulted in higher HM barriers, compared to hydrogen substitution (DMA in black center line). Resonant EDGs (red) lower HM barriers more significantly than inductive EDGs (blue).

Figure 14:
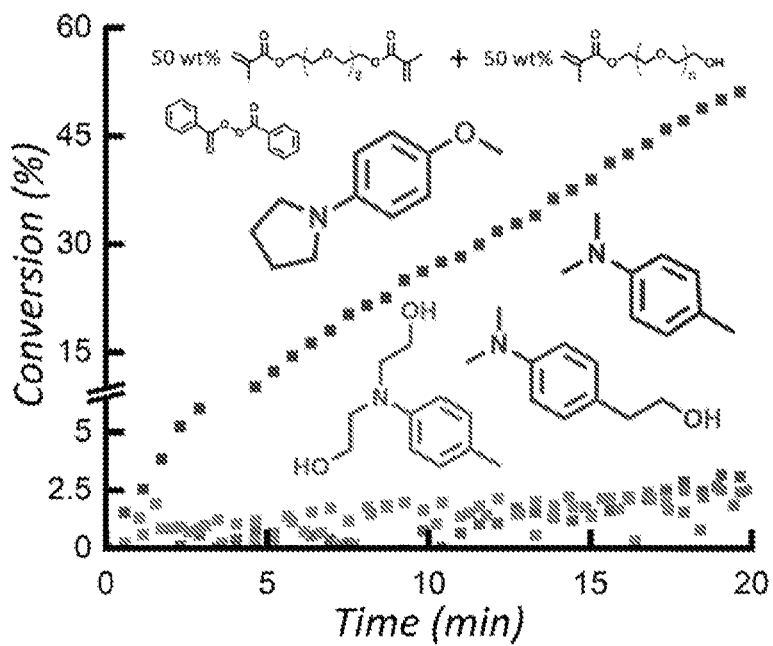
FIG. 14 shows the performance of N-(4-methoxyphenyl) pyrrolidine (MPP) in red, which was discovered through computational screening for APRP in comparison to 2-[4-(Dimethylamino)phenyl]ethanol (DMPEA), 2,2'-(4-Methylphenylimino)diethanol, and N,N-dimethyl-p-toluidine (DMPT) in brown, green, and blue at 0.48 mol % concentration in 50 wt % poly(ethylene glycol) methacrylate and 50 wt % Triethylene glycol dimethacrylate resin.

In view of the insights we've gained, we designed N-(4-methoxyphenyl)pyrrolidine (MPP) that surpassed the redox reactivity performance currently employed amines by a large margin (FIG. 14, the experimental conditions regarding concentration and monomers were changed to accommodate the unprecedented initiating capability of MPP at 0.48 mol % concentrations in methacrylate resin). All the amines that we investigated have only one nitrogen in order to enhance solubility.

Finally, we identified two additional peroxides that are never reported for the use in redox polymerization, which are more efficient oxidants than BPO: phthaloyl peroxide and peroxydicarbonate. Fortunately, phthaloyl peroxide is thermally more stable BPO as well, which makes it a better candidate as oxidant in our photobase-oxidant PI formulation.

Development of Dark Curing Photoinitiators

The focal point of dark curing photoinitiator development is the photo-base-generators that can release redox-active amines appropriately tuned to match the redox potential of an oxidant solubilized in the monomer formulation. Photo-base-generators (PBG) produce amine species in situ, typically by a cascade of photochemical reactions initiated by the absorption of photons and is widely used in epoxide cross-linking and by industry for modifying coatings via a nucleophilic or basic mechanism. The rapid growth of PBGs over traditional photoinitiators lies in their advantage that the former releases an organic nitrogen base as a reactive species that is air stable and inert to causing metal corrosion. Our proposal capitalizes on the strengths of amine stability and inertness as well as the rapid curing and versatility of free-radicals.

Figure 15:
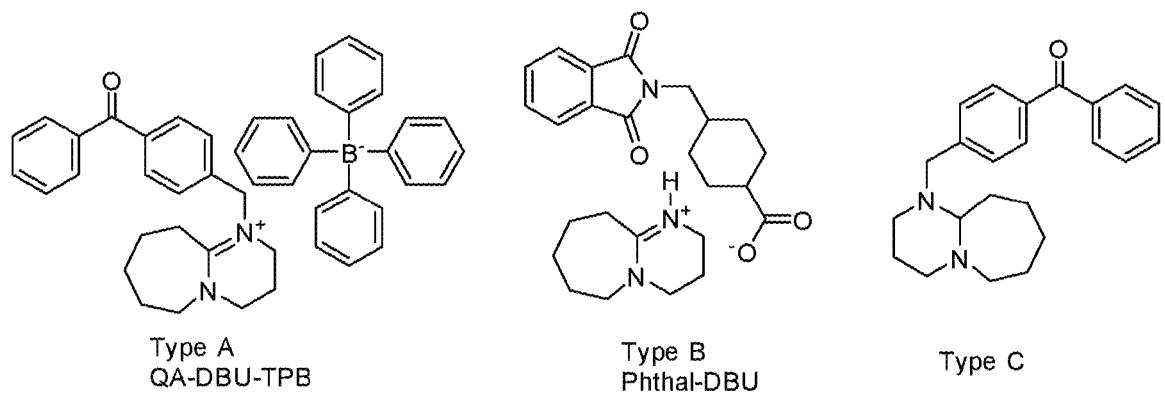
FIG. 15 shows examples of varied classes of photobases.
Figure 16:
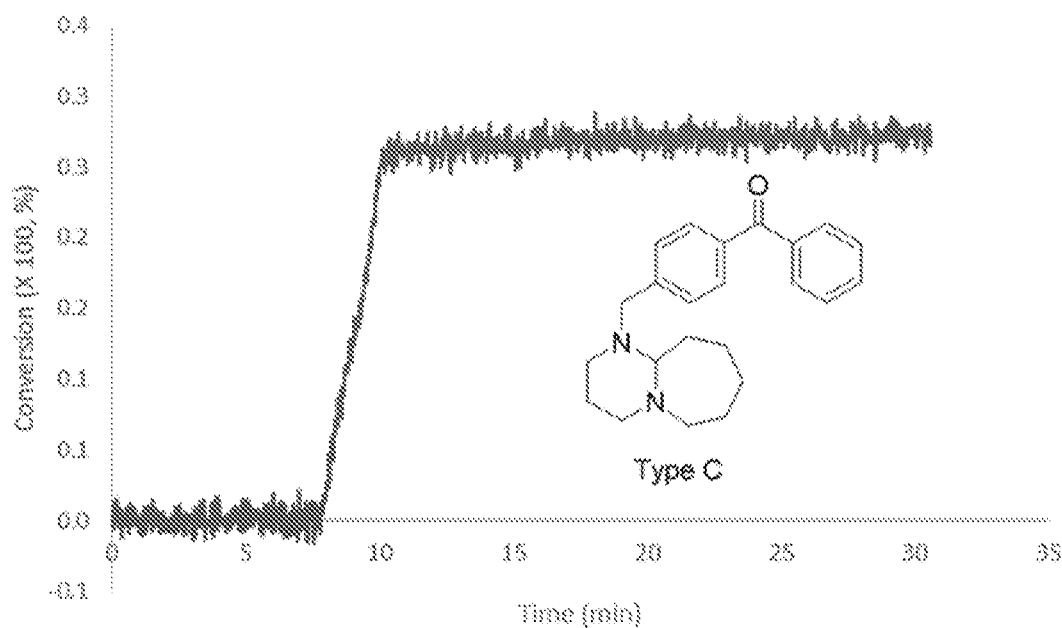
FIG. 16 shows the lack of dark curing in Type C initiation in solvent-free neat resins.

In the existing literature, three types of PBGs have been reported that might be developed for photo-induced redox polymerization (FIG. 15): A) ammonium salts with a covalent bond between amine and chromophore in the presence of electron-donating anions, where the list of candidate photo-releasable amines is not limited by amine nucleophilicity or basicity. But quantum yields differ based on the identity of released amines, again making the mechanistic understanding paramount (our approach here); B) protonated amine photobase with ionic bond between amine and chromophore; and C) neutral amidine-releasing photobase that may offer potential advantages for stability and solubility. We have tried all three types of PBGs, and discarded Type B option as it is less attractive due to ionic bond equilibrium that would inevitably limit shelf-life in addition to being limited to highly basic amines that are not well suited for redox interactions. We also attempted but rejected Type C because it has been found to be inefficient in photo-generation of amines due to their low quantum yield and limited in their synthesis to non-reductive amidines (FIG. 16; it still works as a conventional photoinitiator but without dark curing effect).

With the understanding from amine-peroxide redox polymerization and results from our attempts at various types of PBG, we settled on the PBG molecules described in the following section as our models for the demonstration of effective photo-activated dark curing.

Photo-base-generator/photoinitiator Development

Figure 17:
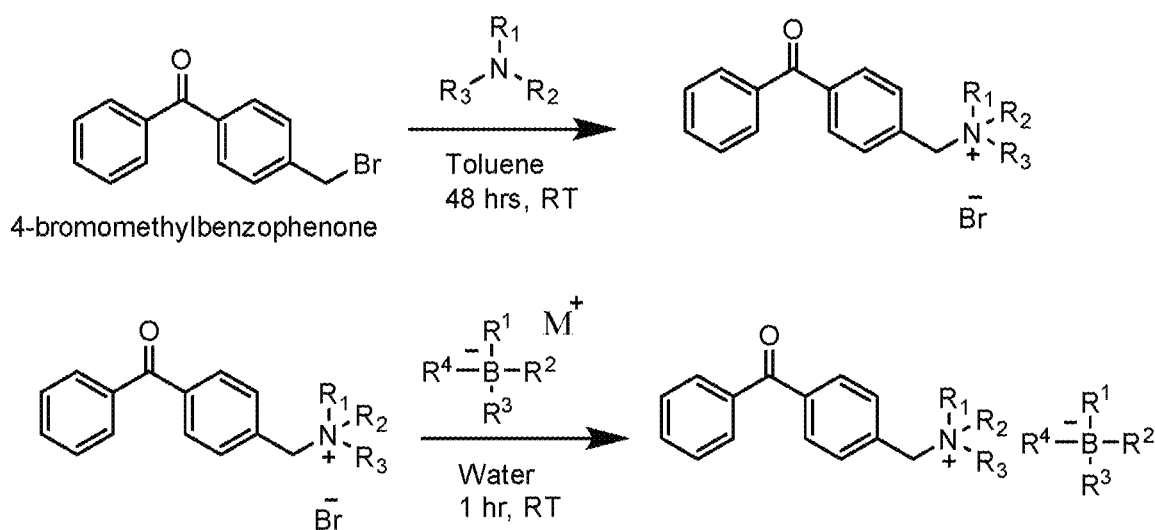
FIG. 17 shows a synthesis of near-UV benzophenone-based photoinitiators.
Figure 18:
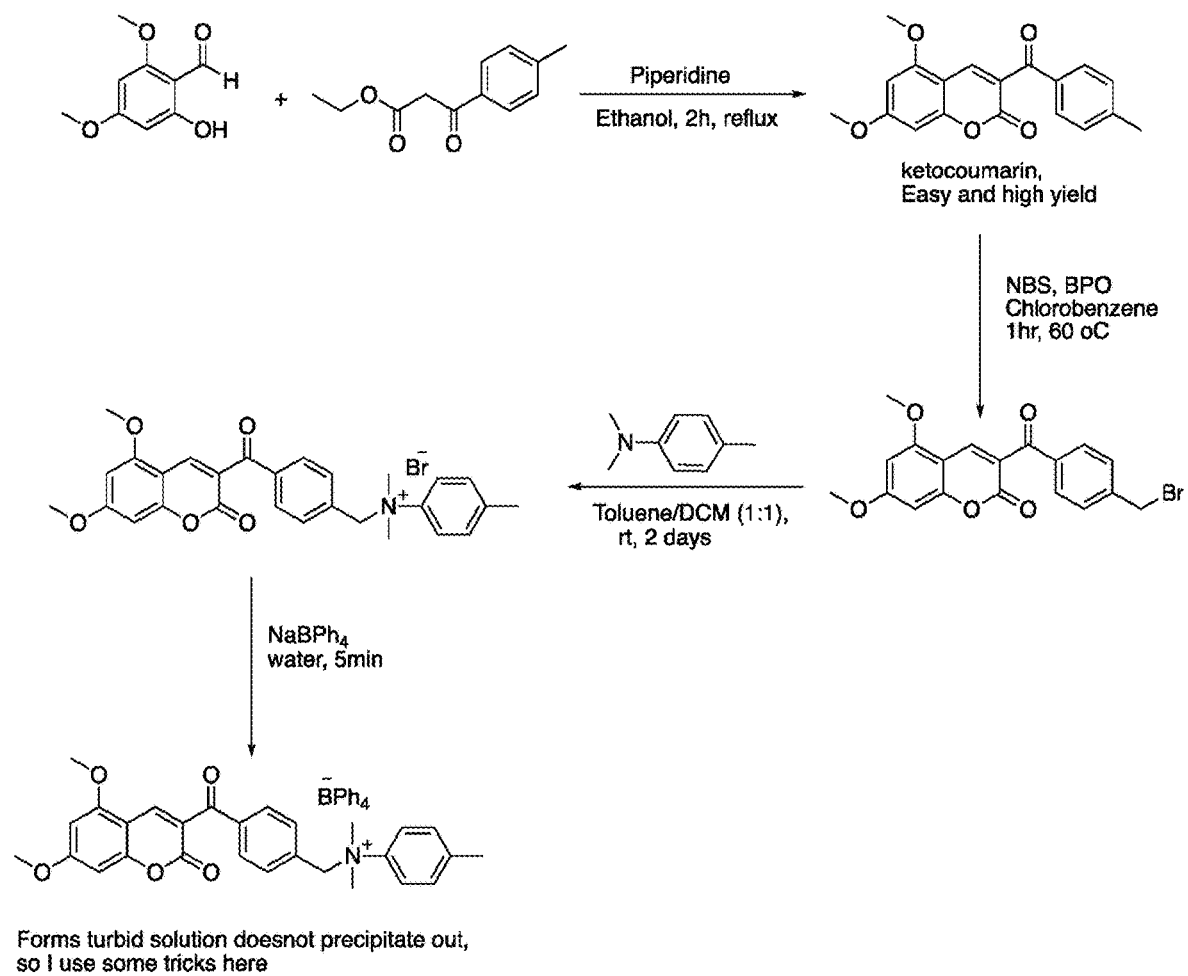
FIG. 18 shows a synthesis of visible light active ketocoumarin photobase photoinitiators.
Figure 19:
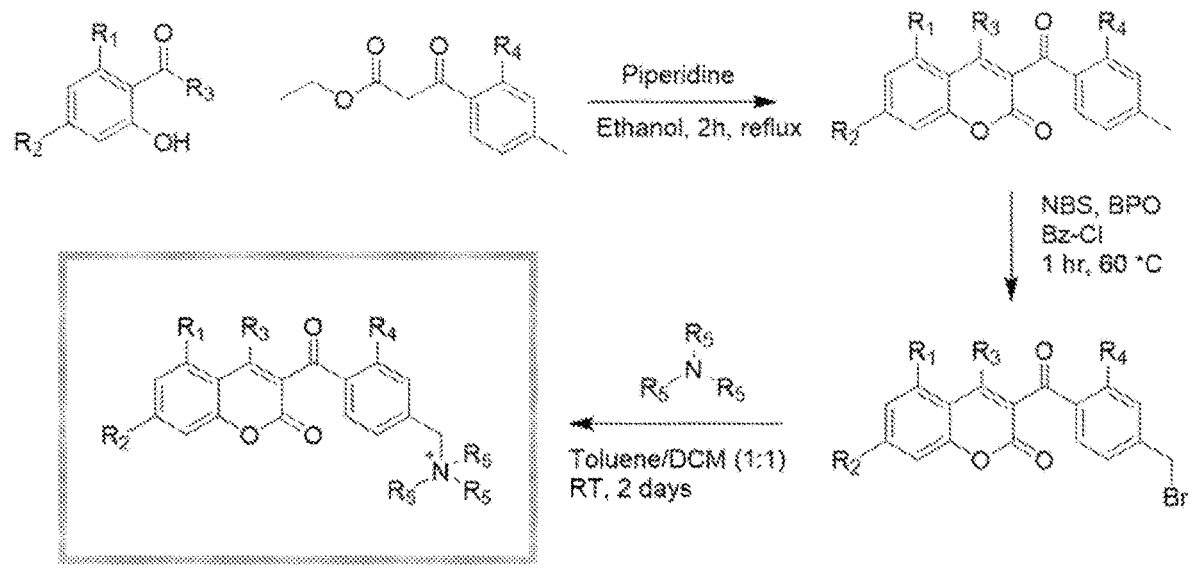
FIG. 19 shows a modular synthesis of the visible light responsive ketocoumarin chromophore.

We designed efficient UV dark-curing photoinitiators via a joint understanding of the photo-base-release mechanism of Type A PBG as well as the redox polymerization mechanism. Its dark-curing capability and various properties are exhibited in the following application with its example synthesis shown in FIG. 17. Another breakthrough in PBG development was the design of ketocoumarin PBG that has high quantum yields of immediate radical generation and photo-base release in the visible range. This PBG represents the first thermally stable, visible range PBG that can photo-release either weak bases with redox capability, such as anilines, or strong bases, such as DBU, without the production of carbon dioxide as a by-product. Furthermore, due to a highly modular synthesis, many physical and photochemical properties can be targeted (FIGS. 18 and 19). For example, if high solubility in non-polar solvents is a target, long alkyl chains like n-butyl groups can be placed in four possible substituent sites (i.e., $R_1$, $R_2$, $R_3$, and $R_4$ in the ketocoumarin chromophore depicted in FIG. 19). Additionally, electron-donating or withdrawing groups can be introduced to rationally modulate quantum yields of direct radical generation and photo-base release by changing excited state electronic structures.

The search for a visible light PBG was conducted in the manner similar to the discovery of efficient amines, using integrated experimental and computational methods. Commonly used visible light thioxanthone and anthraquinone photoinitiators were initially designed with the Type A mechanism in mind. However, these essentially failed to photo-release amines as their triplet energies were lower than the energy required to break a C—$N^+$ bond in the ammonium structure. With this non-obvious mechanistic guidance, we redesigned a PBG with sufficient triplet energy and discovered the ketocoumarin-based photoinitiators that absorb the visible range and provide the desired dual-mode photo-induced initiating capabilities.

Photochemistry of Dark Curing Photoinitiators and Their Physical Properties

Figure 20:
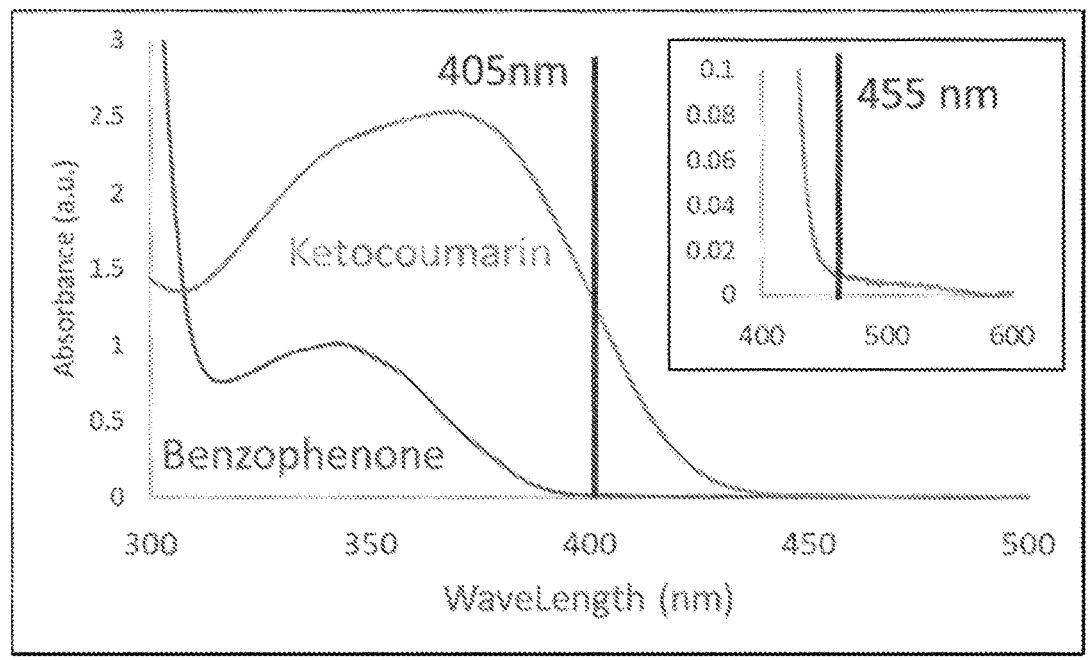
FIG. 20 shows the light absorption of benzophenone- and ketocoumarin-based PBGs (7.5 mM in DMF) that extends to 400 nm and 570 nm, respectively.
Figure 21:
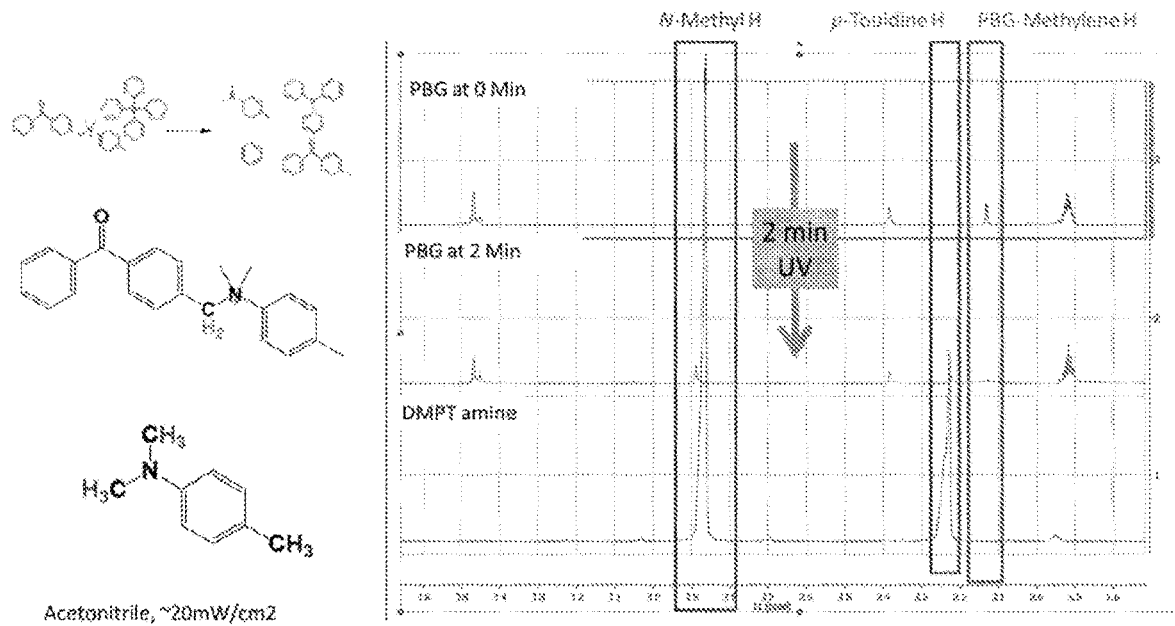
FIG. 21 shows the photo release of amines in a benzophenone-based PBG (i.e, NMR signals for DMPT increased as 365 nm light irradiated the sample).
Figure 22:
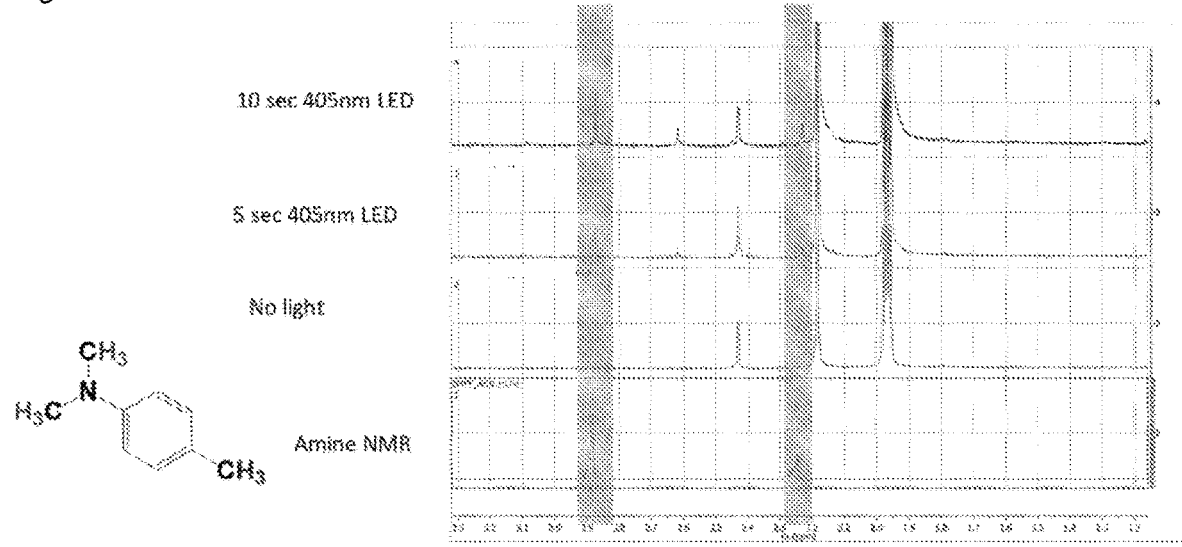
FIG. 22 shows the photo release of amines in a ketocoumarin-based PBG (i.e., NMR signals for DMPT increased as 405 nm light irradiated the sample).
Figure 23:
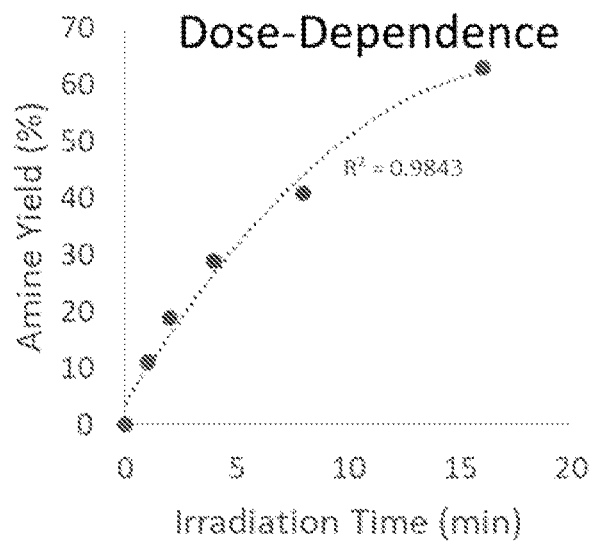
FIG. 23 is shows first-order kinetics of photo-base-release in benzophenone-based PBG, measured by NMR in deuterated acetonitrile.
Figure 24:
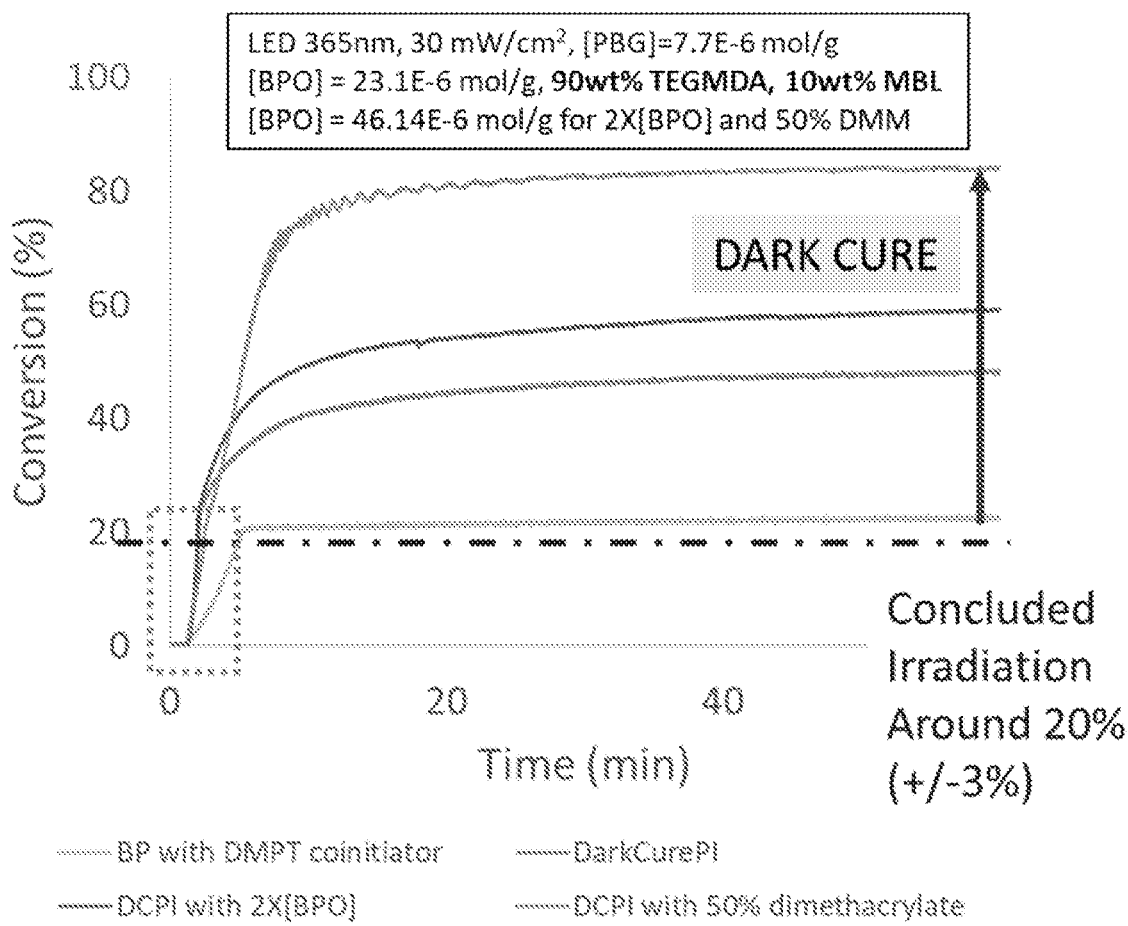
FIG. 24 shows the photo-polymerization profiles of benzopheonone-based dark curing photoiniatior (BP-DMPT/BPO) and conventional photoinitiators (BP with DMPT coinitiator) under identical photocuring conditions in crosslinking resins without solvent, using 365 nm LED.

Wavelengths that photoinitiators can absorb have great implications on photopolymer applications. Although UV-absorbing photoinitiators have been widely used, visible-absorbing photoinitiators are desirable due to their potential for significantly greater light penetration depth, more affordable light sources, and less damaging irradiation to cells. We demonstrate herein that two embodiments of our PBGs can meet the needs of most photopolymer applications, covering wavelengths from the UV to the visible range for light absorptions (FIG. 20). We also verified that these two PBGs indeed released the attached amine by monitoring NMR signal changes (FIG. 21 and FIG. 22). Furthermore, the photo-releasing behaviors followed first-order reaction kinetics (FIG. 23). Without being bound to a particular theory, this may be due to tight-binding of electron-donor and -acceptor by electrostatic force, which would explain the highly efficient nature of radical generation and photo-base release. Additionally, the data from cyclic voltammetry indicated that the electron-transfer is irreversible without a possibility of back electron-transfer, making these PBGs very photon-efficient. Lastly, each of our formulations was tested with a differential scanning calorimeter (DSC) to confirm their shelf-stability. We used a monomer sample with BPO only as a reference, which is appropriate since there are many commercial products that contain BPO have confirmed shelf-stability of up to two years. We ran the DSC under helium gas purge with a 10° C. per minute heating ramp from 30 to 120° C., using 10-15 mg of samples that were directly used in our dark curing demonstrations, namely in FIGS. 24, 25, and 26. FIG. 24 shows the various degrees of dark curing achieved with the tested dark curing photoinitiators while the conventional photoinitiators did not show any significant dark curing. The results show that the onset of polymerization for the reference BPO sample was at 91.8° C. while that for our complete dark curing formulation was at 108.4° C., indicating that this dark curing formulation can be expected to offer shelf-life stability at least comparable to products that contain BPO as a component.

Further Dark Curing Results

Figure 2:
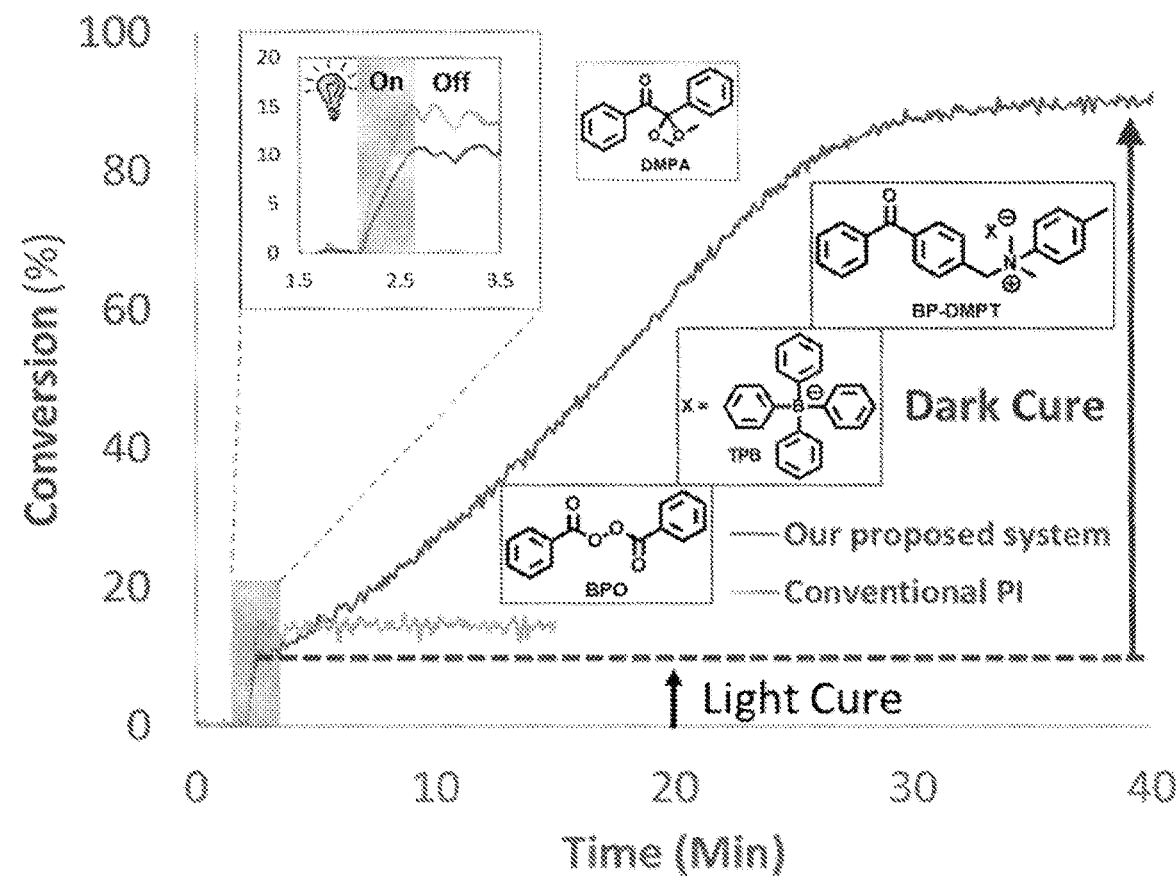
FIG. 2 shows photo-polymerization profiles of dark curing photoinitiator (BP-DMPT/BPO) and conventional photoinitiators (DMPA; 2,2-dimethoxy-2-phenylacetophenone) under identical photocuring conditions in crosslinking resins without solvent. Brief irradiation (yellow box) for 30 seconds resulted in a similar degree of light cure for both initiators (demonstrating efficient direct production of radicals) yet when the light was stopped at a low conversion, the dark curing photoinitiator continued to polymerize over time without any additional light exposure in contrast to the immediate plateauing of monomer propagation in the DMPA-initiated analog.

Beyond the singular example of dark curing in FIG. 2, this section contains several examples of dark curing in various conditions by benzophenone- and ketocoumarin-based PBGs with occasional comparison to conventional photoinitiators to delineate the difference between our new technology and the current technology. FIG. 24 demonstrates the dark curing ability of benzophenone-based PBG with BPO oxidant in 90 wt % di-methacrylate and 10 wt % mono-methacrylate, using 365 nm LED. BP with DMPT co-initiator was used as a conventional Norrish Type 2 photoinitiator, shown as yellow in FIG. 24. When the irradiation was concluded at 20% conversion, the conventional photoinitiator achieved a few percent of dark curing over 60 minutes of monitoring while extensive dark curing can be observed in our initial formulation shown as green in FIG. 24. Increasing BPO concentration resulted in fa aster dark curing rate, reaching the vitrification-limited conversion more quickly (Blue in FIG. 24). Reducing crosslinking density by changing the resin to 50 wt % mono-methacrylate and 50 wt % di-methacrylate induced even faster and more extensive dark curing due to increased diffusional rates of amine and peroxide leading to higher rates of redox reactions (Orange in FIG. 24).

Figure 25:
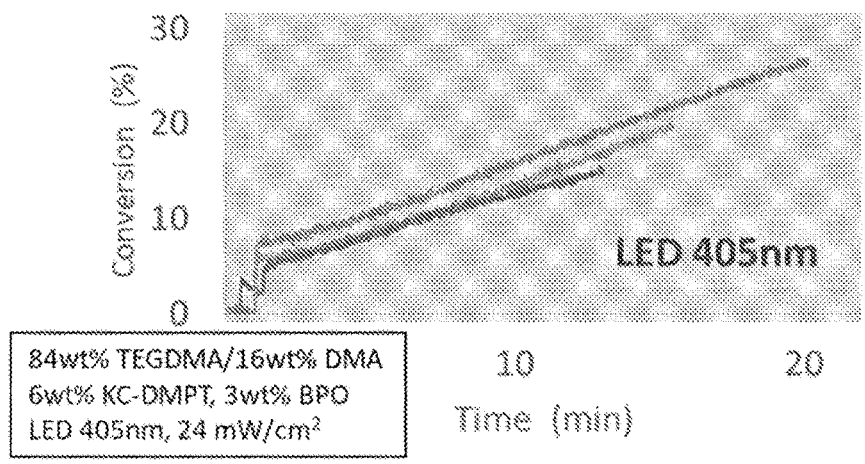
FIG. 25 shows photopolymerization profiles of ketocoumarin-based dark curing photoinitiators (KC-DMPT/BPO) in crosslinking resins without solvent, using 405 nm LED.
Figure 26:
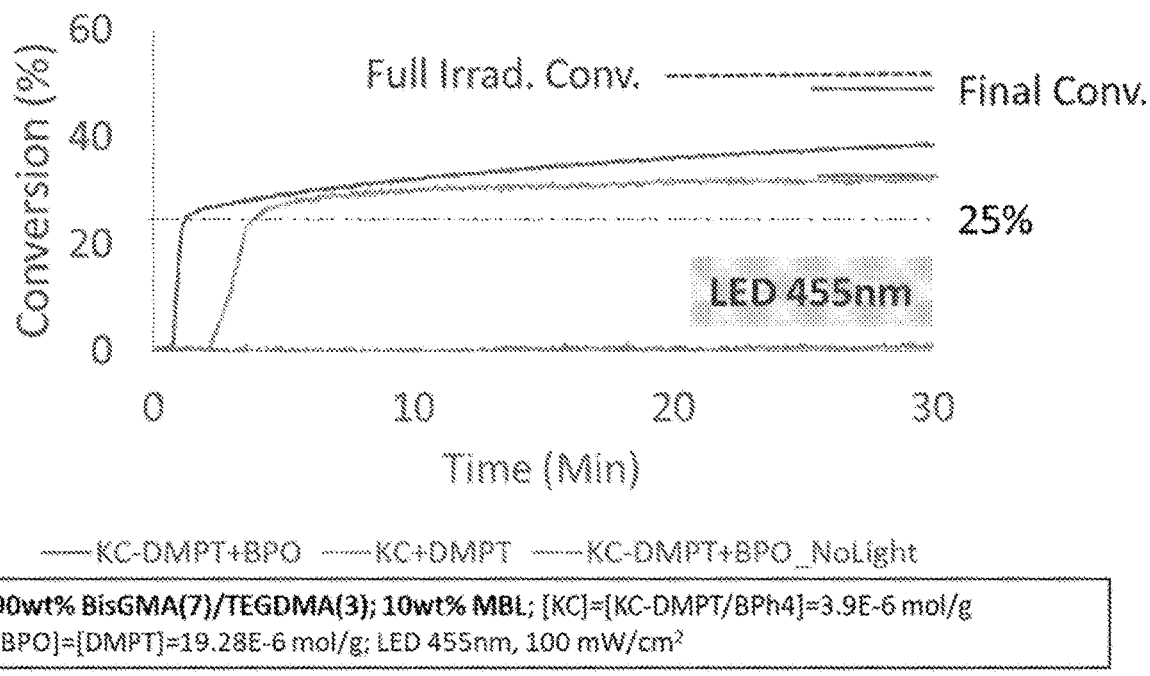
FIG. 26 shows photo-polymerization profiles of our ketocoumarin-based dark curing photoinitiators (KC-DMPT/BPO) and conventional photoinitiators (KC with DMPT coinitiator) under identical photocuring conditions in crosslinking resins without solvent, using 455 nm LED.

Similar dark curing abilities can be found in ketocoumarin-based PBGs, when irradiated with visible light. First, irradiation with 405 nm LED induced rapid photopolymerization process, indicated by a sharp increase in conversion during irradiation. However, when the irradiation stopped, slower yet continuous conversion was observed, indicating the dark curing capability (FIG. 25). This exciting result extended to an even higher wavelength at 455 nm (FIG. 26). This demonstration was in highly viscous and crosslinking resin, commonly used for dental composite applications. The orange plot in FIG. 26 demonstrates that the complete dark curing formulation is stable over time without intentional exposure. The grey plot in FIG. 26 is the control (i.e., conventional Norrish type 2 photoinitiator, similar to the one in FIG. 24). When irradiation stopped at 25% conversion, the control reached 30% conversion due to trapped radical in highly viscous and crosslinking resin; however, this did not continue, effectively limiting its post conversion within 5%. The blue plot in FIG. 26 is the ketocoumarin-based dark curing initiator. Within 30 minutes, it did not differ significantly from the control. However, over 2 hours, the final conversion is statistically no different from the full conversion that was achieved with continuous irradiation. With these examples, we convincingly demonstrated the difference between our dark curing photoinitiators and conventional photoinitiators.

Continuous Development for Better Dark Curing Initiators

Figure 27:
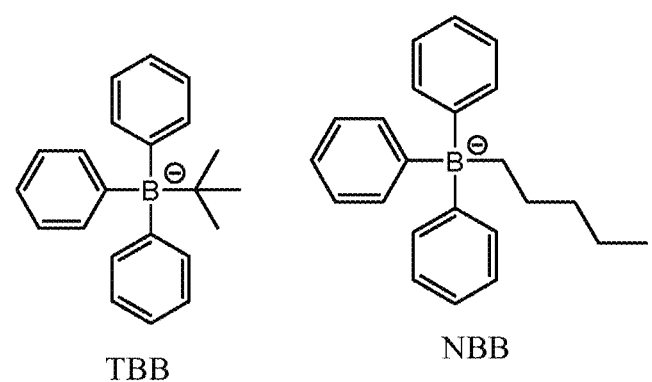
FIG. 27 shows two efficient electron-donating borate counter ions for use in photo-base complexes.

In order to increase photopolymerization efficiency and solubility, we designed new mixed alkyl-aryl borate salts. Based on our initiating systems, during light exposure, rapid photopolymerization proceeds from radical production that results from the degradation of the borate salt as a result of electron donation. Therefore, more reducing borates will increase the photopolymerization rate. By substituting one of the phenyl groups, we discovered more efficient photoinitiators (FIG. 27). Tetraphenyl borate (TPB) is much less reducing than n-butyl triphenyl borate (NBB) and t-butyl-triphenyl borate (TBB) evidenced by their ionization potential (TPB: 7.23 eV, NBB: 7.09 eV, TBB: 6.94 eV). Note that lower ionization potential signifies the greater likelihood of electron donation. We also discovered that incorporation of alkyl groups instead of phenyl groups resulted in greater solubility in acrylic resins. Another result of photo-induced electron transfer is the aforementioned release of amines. The increased rate of electron transfer also results in larger number of released amines, which in turn enhances the dark curing rate. A selection of varied chromophores, anions, and amines were used to construct a library of photo-base complexes as detailed in Table 2. Some but not all of photo-base complexes in Table 2 are effective dark curing initiators.

TABLE 2

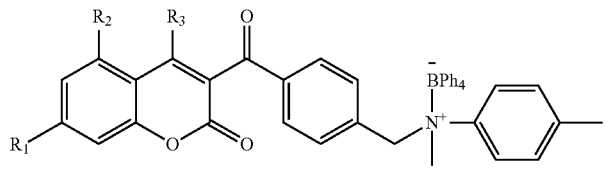

wherein $R_1 = R_2$ and are selected from the group consisting of —H, —OCH$_3$,

   where $R^2$ is a linear or branched alkyl group, and   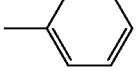 , and $R_3$ is selected from the group consisting of   —H,   —OH,   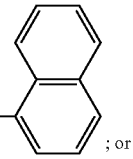 ,   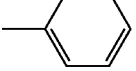 ; or wherein $R_1 \neq R_2$ and are selected from the following table

| $R_1$ | $R_2$ |
|---|---|
| —OCH3 | —H |
| —NR', where R' = H, a linear or branched alkyl group, or —HAc | —H |
| —SR''' where R''' = linear or branched alkyl group, or —COCH$_3$ | —H |
| —O—C(=O)—R''  where R'' = linear or branched alkyl group | —H |
| —OH | —H |
| —H | 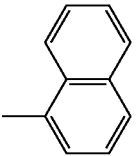 |
| —H | 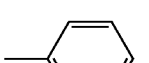 | and $R_3$ is selected from the group consisting of   —H,   —OH,   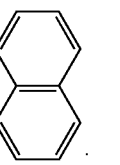 .

TABLE 2-continued
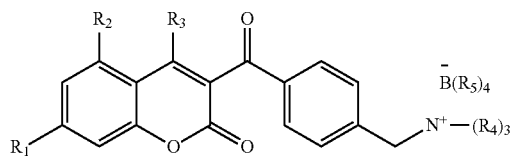
wherein $R_1$, $R_2$, $R_3$ are selected as mentioned above, the amine cation is selected from the following
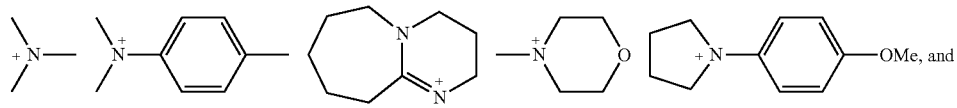
the borate cation is selected from the following
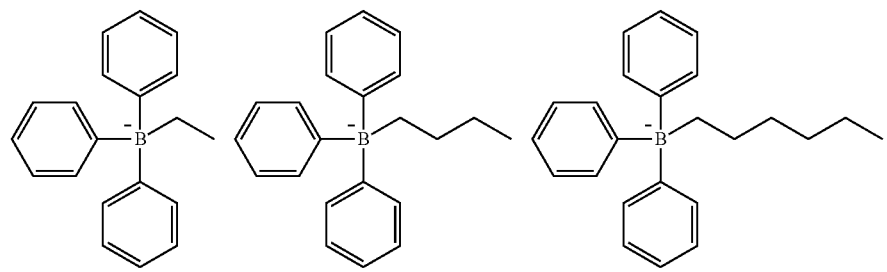 [SMILES: CC[B-](c1ccccc1)(c1ccccc1)c1ccccc1 ; CCCC[B-](c1ccccc1)(c1ccccc1)c1ccccc1 ; CCCCCC[B-](c1ccccc1)(c1ccccc1)c1ccccc1]
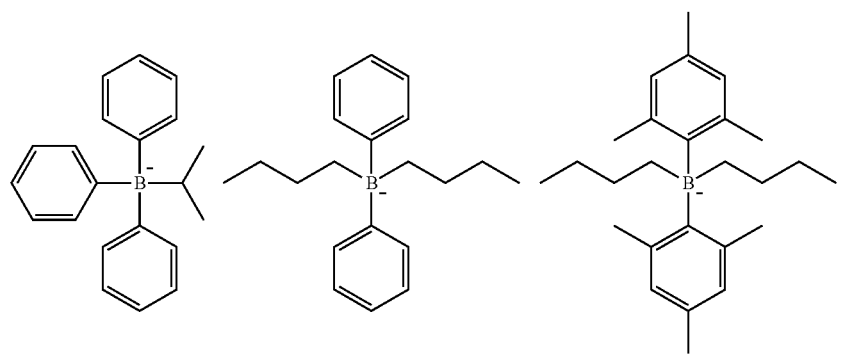 [SMILES: CC(C)[B-](c1ccccc1)(c1ccccc1)c1ccccc1 ; CCCC[B-](CCCC)(c1ccccc1)c1ccccc1 ; CCCC[B-](CCCC)(c1c(C)cc(C)cc1C)c1c(C)cc(C)cc1C]
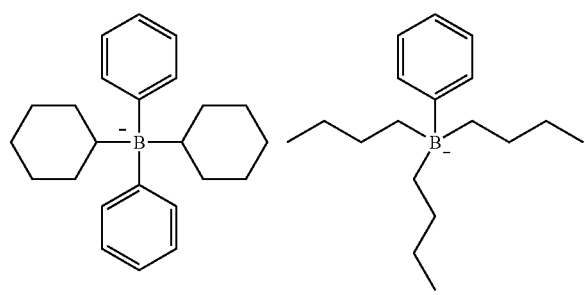 [SMILES: c1ccc([B-](c2ccccc2)(C2CCCCC2)C2CCCCC2)cc1 ; CCCC[B-](CCCC)(CCCC)c1ccccc1]

TABLE 2-continued

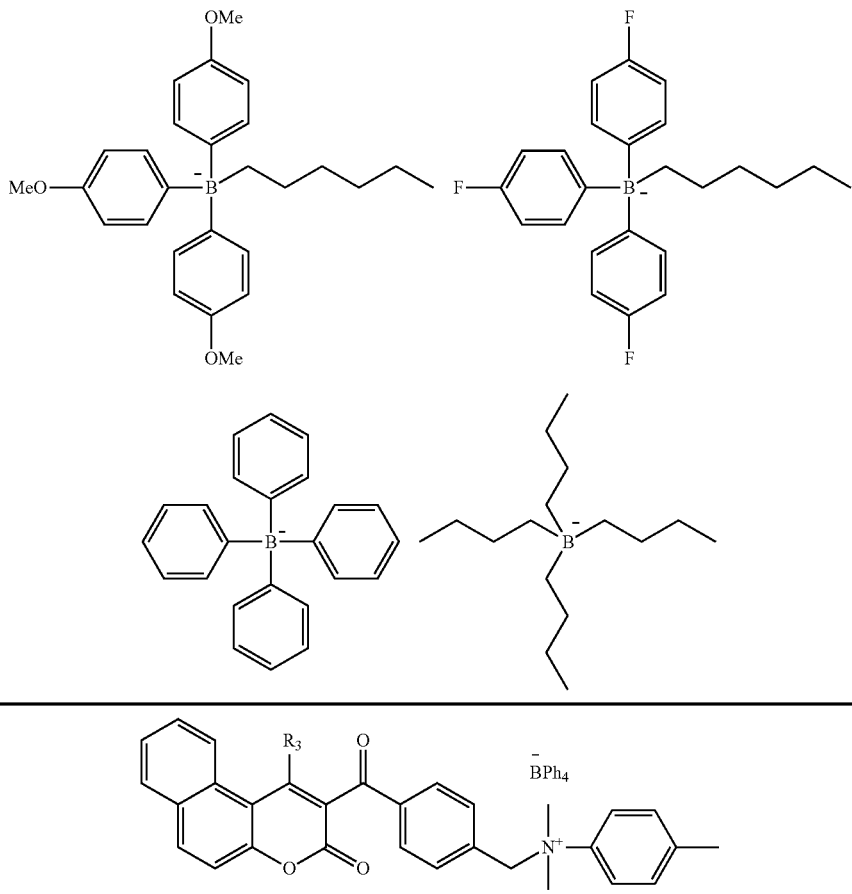

wherein $R_3$ is selected as mentioned above ($R_1$ is H and $R_2$ is a constituent of a fused aryl).* The ketocoumarin constituent is 3,4-benzo-ketocoumarin.

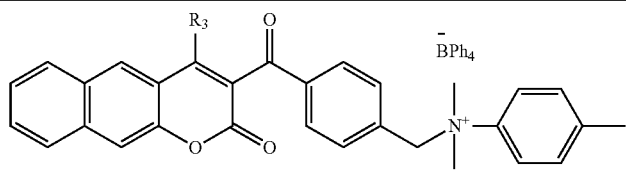

wherein $R_3$ is selected as mentioned above ($R_1$ is a constituent of a fused aryl and $R_2$ is H).* The ketocoumarin constituent is 4,5-benzo-ketocoumarin.

*The absorption of the photo-base generators in which R1 or R2 is a constituent of fused aryl are red-shifted compared to the other compounds set forth in this table.

To give greater detail on the non-obvious selection of the various structural components that are integrated together to produce the highly photon-efficient and reaction rate tunable photobase-redox initiator system, we provide the following design details, which allow control of the initial radical production during the direct photo-activation step and the associated latent radical production to allow highly effective dark cure initiation extending well beyond the irradiation interval. The benefits of this approach are that it is a highly photon efficient initiation process that allows the redox curing process to either augment the photocuring process when high redox reaction rates are involved or to provide a second stage of radical production extending beyond the light exposure where the dark cure rate can be manipulated as desired for a particular application.

Figure 28:
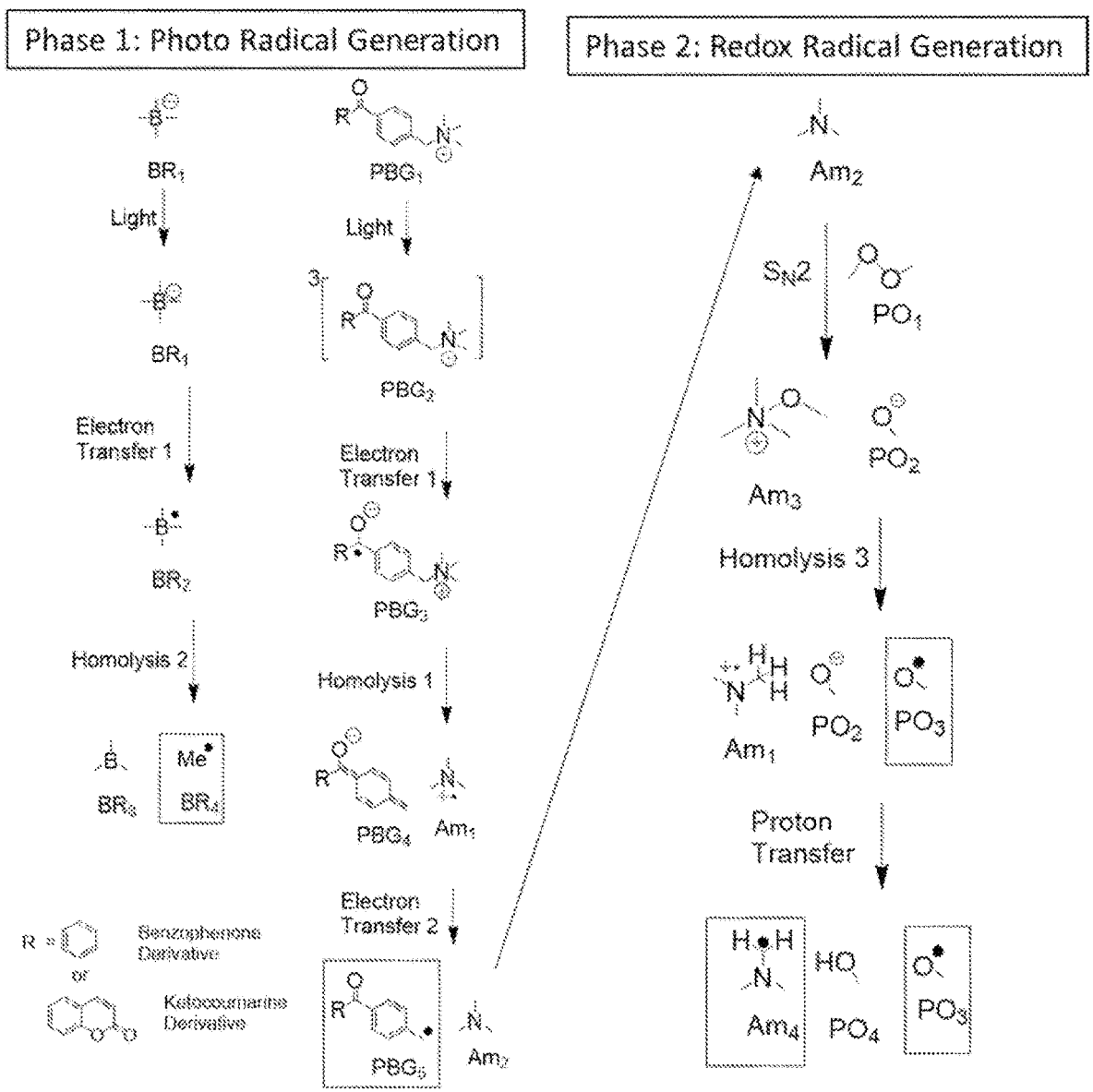
FIG. 28 depicts total radical generation in two phases of photo radical generation and redox radical generation for a photoinitiator embodiment of the present invention.

Overview of the Total Radical Generation Process with Tunable Photobase-redox Initiating Systems for UV and Visible Light Activation Here, we delineate our strategy to design purpose-built dark curing photoinitiators for a variety of applications. First, we describe the total radical generation split into two phases in FIG. 28. Phase 1 (photo radical generation) describes immediate radical generation during irradiation, generating two viable radicals, namely benzylic radical derivative ($PBG_5$) and alkyl radical derivative ($BR_4$). Phase 2 (redox radical generation) describes latent radical generation post-irradiation, which produces two more viable radicals, alpha-aminoalkyl radical ($Am_4$) and alkoxy radical ($PO_3$). These initiating radicals are boxed. R can be benzophenone or ketocoumarin derivatives. For simplicity in this example, methyl substitution was used here for amine, peroxide, and borate structures, but structural variations as described below can significantly alter the reactivity and overall quantum efficiency.

Despite the complex mechanism, our dark curing process remains highly efficient, as shown in previous examples. Overall yield of radicals is four, making it highly photon-efficient in comparison to conventional photoinitiators that typically lead to one or two viable radicals. It should be noted that Phase 1 reactions are fundamentally different from Norrish Type II reactions in four ways. 1) Only electron transfer (ET1) is involved in radical generation instead of sequential ET followed by proton transfer in Norrish Type II, making our PI more efficient. 2) Ensuing homolysis 2 to make a radical ($BR_4$) is simultaneous, preventing any back-electron transfer process from occurring while back-electron transfer processes are often encountered in Norrish Type II initiation that lowers the quantum yield, because proton transfer process is slower than electron transfer process. 3) Electron transfer 1 is accelerated due to electrostatic attraction between ET donor and acceptor that results in close proximity with each other in relatively non-polar resin, constituting tight ion pair. In contrast, the reaction rates in Norrish Type II have to partially depend on diffusional rates determined by thermal energy, making it less efficient in more viscous resins. 4) Finally, the radical from photoinitiator moiety ($PBG_5$) that is similar to radicals from styrene, is also active initiating species unlike non-initiating ketyl radical in Norrish Type II. These differences distinguish our photoinitiators in addition to the photobase-generation that we can use to do additional chemistry.

Amine species that will undergo redox radical generation are based on the simultaneous homolysis 1 reaction and electron transfer 2 reaction between $PBG_4$ and $Am_1$. The electrostatic attraction of donor and acceptor affects the electron transfer 2 reaction resulting in efficient generation of the reactive amine species ($Am_2$). $Am_2$ undergo $S_N2$ reaction and Homolysis 3 to generate the third initiating radical, alkoxy radical ($PO_3$). The barrierless proton transfer results in alpha-aminoalkyl radical ($Am_4$). Most of the elementary reaction we described can be modulated by various functional groups, suggesting that we are able to design purpose-built dark curing photoinitiators to meet a wide range of applications. We describe some of the approaches to achieve desired photoinitiators, rationalized with our advanced understanding of these processes.

Phase 1 Photo Radical Generation

Chromophore

The primary goals of chromophores in this mechanism are to absorb wavelength, to oxidize borate anions, release amine radical cation and reduce it to active amine, while also delivering an initiating radical at the end of the mechanistic process. We base our initiators on benzophenone and ketocoumarin chromophores. These chromophores are well-studied as photosensitizers and Norrish type II photoinitiators. Their UV-Vis absorption can expand further into visible range by functionalizing particularly the ketocoumarin PI with electron-donating group such as conjugative (e.g., vinyl, phenyl, and naphthyl), amino (e.g., julolidine, amino, and (di)alkylamino), or alkoxy groups. However, any amino functional groups must not be used as they may react with peroxide and deteriorate the shelf-stability of the dark curing formulation.

Also, naphthyl and phenyl groups may reduce the solubility of the photoinitiator in common monomers. But in some cases, these entended conjugation substitutions can be desired, notably in styrene or other highly aromatic monomers.

With this insight, we have chosen methoxy substitution to increase the UV-vis absorption while also enhancing solubility of the photobase in nonpolar monomer formulations. Alkoxy groups with longer or larger alkyl chains will even increase the solubility further without compromise in the photochemical properties. Vinyl substitution will increase the ability of the photoinitiator to be covalently incorporated into the polymer in cases of residual free photoinitiator or photodegraded molecules that do produce active radicals themselves.

Electron-withdrawing group (EWG) will cause similar red-shifting effect, but to a smaller degree based on Woodward's rule. It's likely that EWG-substituted PI will be more photo-active because these chromophores are electron-acceptors in Electron Transfer 1 and EWG-substitution will lower their LUMO levels by making the chromophores more electron poor. However, the chromophore as $PBG_4$ must be able to undergo electron transfer 2 as an ET donor. This complexity of chromophores acting as both acceptor and donor in the mechanism renders the dark curing photoinitiator design particularly difficult without the mechanistic understanding of photobase-release and methods to calculate relevant photochemical values. Again, this is why we chose methoxy substitutions as a demonstration since we understood that the specific borate anion we used can reduce the chromophore with methoxy substitutions for Electron Transfer 1 while the resultant $PBG_4$ would be able to reduce $Am_1$ of amine that we used.

FIG. 29 shows exemplary chromophores with the associated computationally derived photochemical properties. Most of KC structures absorb at similar wavelength ranges, except for conjugative substitutions. Low LUMO levels are correlated with higher photopolymerization rates, as higher electron transfer rates cause more efficient radical generation. All $PBG_4$ HOMO energies are capable of reducing most aromatic amine and some non-aromatic species except for tetramethoxy-KC.

Borate Anions

The primary goals in the selection of borate anions as the counter ion to the positively charged amine cation are to reduce the chromophore as an ET donor in Electron Transfer 1 and then to generate an additional radical during irradiation in Homolysis 2. Borate anions with various substitutions will affect these two processes. Fortunately, these two goals are positively correlated. Substitution of tetraphenyl borate with any alkyl group will make the borate more reducing while also generating alkyl radical at a higher rate. More highly substituted alkyl group (i.e. tert-butyl) will be more effective than less substituted alkyl group (n-butyl group), as high degree of substitution increases inductive electron-donating effect. Nearly all alkyl radicals will initiate vinyl monomer polymerization so increasing the rate of radical release directly corresponds to increases in the photopolymerization rate. As a result, alkyl-substituted borate anions will enhance the photobase-release as well as direct photopolymerization. Concomitantly, increase of alkyl substitution or decrease of aromatic substitution will increase the photobase solubility in common monomers.

FIG. 30 shows exemplary borates with the calculated HOMO levels. Higher HOMOs as in tetra-4-methoxy-phenyl or tetra-n-butyl borates are correlated with higher reducing powers that result in faster photopolymerization rates as well as faster photobase-release. Incidentally, increased alkyl group contribution in borate anions lead to higher solubility of the photobase in common monomer.

Amine

The primary goals in the selection of the covalently bound ammonium salt component of the photobase are the potential for photo-release of amine from the chromophore, the ability of the released species to be reduced from amine radical cation to active free amine, and then the ability of the free amine to react with an oxidant (peroxide in this example) to elicit the non-light dependent amine-peroxide latent radical generation. The identity of amine can affect the quantum yield for photobase-release. Within the Phase 1 reaction framework, the choice of amine does not affect light-absorption, excitation, and Electron Transfer 1, but it can affect the Homolysis 1 and Electron Transfer 2 reactions. If the bond strength of C—$N^+$ bond in $PBG_3$ is too strong, the photoexcitation energy will dissipate as heat instead of breaking the bond to release the amine. The bond strength will be dependent on amines, as the increased stability of resultant amine radical cations are correlated with weaker bonds. In that regard, aromatic amines are best suited as bases to be released; however, other non-aromatic amines can also be released but with lower efficiency. An important aspect is that this stability of amine radical cation should be carefully considered so that $PBG_4$ is able to reduce it, which again requires the understanding of the relationship between chromophore and amine within the photobase-release mechanism to rationally produce effective initiating systems.

Phase 2 Redox Radical Generation

Amine

In Phase 2, the liberated amine reacts with peroxide or other appropriate oxidant to induce the latent radical generation or dark cure component of the photo-activated radical initiation process. The first reaction, SN2, indirectly determines the induction time. The faster the SN2 reaction, the faster the resultant intermediates can undergo Homolysis 3 and the faster the latent radical generation. However, in cases where long induction time is desired, the use of amines that have large steric hindrance effects in their N,N-substitutions (i.e. isobutyl groups) will be helpful. On the other hand, dimethyl and pyrrolidine undergo the fastest SN2 reactions. High stability of amine radical cation ($Am_1$) causes fast Homolysis 3. With our ability to calculate kinetic properties of amines in each reaction step, we identified and experimentally confirmed our ability to integrate various amine structures into the photobase that then liberate those different amines to controllably vary the latent redox reaction rates. This enables us to modulate dark curing rates in Phase 2 largely independent of the direct photoinitiation rate associated with Phase 1.

FIG. 31 shows exemplary amines that are active in amine-peroxide redox polymerization with reaction rates and pKa. Amines are organized in an increasing order of redox radical generation rates except for N,N-ethoxy-4-methylaniline that should be used when long induction time is desired. If base-catalyzed reactions are desired, N-methyl morpholine or N-methyl pyrrolidine can be used. Such figure demonstrates our ability to accurately calculate kinetic properties and apply them to the design of dark curing photoinitiators that then demonstrate experimentally validated results in terms of polymerization rates.

Peroxide

Peroxide reacts with amine species for the latent radical generation in phase 2 of our photobase-redox initiating system. Since the peroxide is uniformly and freely distributed in the formulation, the stability of peroxide is an important consideration for formulation shelf-stability in addition to its potential for undesired reactivity with the ammonium salt in the photobase compound as well as the desired reactivity with the photo-released amine. From our studies of most commercial and non-commercial peroxides, only a few peroxides can undergo redox reaction with amine. Benzoyl peroxide is commonly used. However, dialkyl-acyl-peroxide (i.e., dilauroyl peroxide) undergoes the redox reaction with a similar reactivity. We also report that diperoxy carbonate and phthaloyl peroxide will readily undergo the redox reaction. Diperoxy carbonate is typically thermally less stable than benzoyl peroxide but will undergo faster redox reaction. Lastly, phthaloyl peroxide has advantages of both higher thermal stability as well as high redox reaction rates, which has not been reported previously.

FIG. 32 shows exemplary peroxides with various computational redox reactivities and thermal stability. Benzoyl peroxide is essentially the only peroxide that has been used for redox polymerization. It has a decent redox reactivity with a good thermal stability. For fast dark curing formulations, phthaloyl peroxide would be a better choice with higher redox reactivity and thermal stability. However, based on specific applications, other peroxides and other oxidants can be potentially be used as well.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A quaternary ammonium salt comprising a chromophore constituent, a tertiary amine cation constituent connected to the para-position of the chromophore constituent via a methylene linkage, and a borate anion constituent, wherein chromophore constituent is a 3-ketocoumarin constituent and the quaternary ammonium salt has the formula (I)

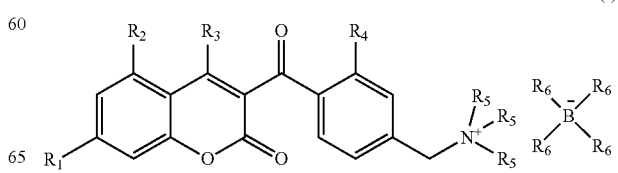

(I)

wherein:
R₁ and R₂, identical or different, are independently selected from the group consisting of —H, —OH, linear or branched $C_1$-$C_8$-alkoxy group,

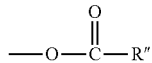

where R" is a linear or branched $C_1$-$C_8$ alkyl group, unsubstituted or substituted -phenyl group, unsubstituted or substituted -naphthyl group, unsubstituted or substituted -vinyl group, -halogen, and halogenated $C_1$-$C_8$-alkyl group;

R₃ is selected from the group consisting of independently selected from the group consisting of —H, —OH, linear or branched $C_1$-$C_8$-alkoxy group, -halogen, and halogenated -alkyl group;

R₄ is selected from the group consisting of independently selected from the group consisting of —H, —OH, linear or branched $C_1$-$C_8$-alkoxy group, -halogen, and halogenated $C_1$-$C_8$-alkyl group;

R₅, identical or different, is independently selected from the group consisting of linear or branched $C_1$-$C_8$ N-alkyl group; hydroxyl-substituted $C_1$-$C_8$ N-alkyl group; fused 5-7 member heterocyclic ring; and unsubstituted or substituted aromatic ring, wherein the substituent on the aromatic ring is selected from the group consisting of linear or branched $C_1$-$C_8$ alkyl group and linear or branched $C_1$-$C_8$ alkoxy group; and R₆, identical or different, is independently selected from the group consisting of linear or branched $C_1$-$C_8$ alkyl group, and unsubstituted or substituted aromatic ring wherein the substituent on the aromatic ring is selected from the group consisting of linear or branched $C_1$-$C_8$ alkyl group, linear or branched $C_1$-$C_8$ alkoxy group, and halogen.

2. The quaternary ammonium salt of claim 1, wherein each alkoxy group is independently selected from the group consisting of methoxy and butoxy.

3. The quaternary ammonium salt of claim 2, wherein R₃ is —H or linear or branched $C_1$-$C_8$-alkoxy.

4. The quaternary ammonium salt of claim 1, wherein R₃ is —H.

5. The quaternary ammonium salt of claim 1, wherein:
the substituted -phenyl group has one or more independently selected substituents selected from the group consisting of linear or branched $C_1$-$C_8$ alkyl group, linear or branched $C_1$-$C_8$-alkoxy group, -halogen, and halogenated $C_1$-$C_6$-alkyl group;
the substituted -naphthyl group has one or more independently selected substituents selected from the group consisting of linear or branched $C_1$-$C_8$ alkyl group, linear or branched $C_1$-$C_8$-alkoxy group, -halogen, and halogenated $C_1$-$C_6$-alkyl group; and
the unsubstituted vinyl group is $C_2$ and the substituted vinyl group is an extended vinylene up to $C_{10}$.

6. The quaternary ammonium salt of claim 1, wherein at least one of the R₅ groups is the substituted aromatic ring.

7. A quaternary ammonium salt comprising a chromophore constituent, a tertiary amine cation constituent connected to the para-position of the chromophore constituent via a methylene linkage, and a borate anion constituent, wherein chromophore constituent is a 3-ketocoumarin constituent and the quaternary ammonium salt has the formula (I) or the chromophore constituent is a benzophenone constituent and the quaternary ammonium salt has the formula (II)

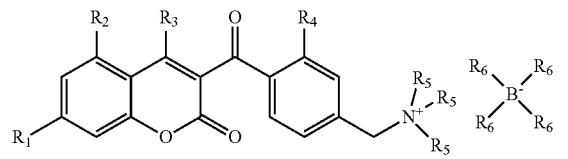

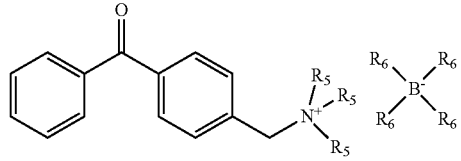

wherein
R₁ and R₂, identical or different, are independently selected from the group consisting of —H, —OH, linear or branched $C_1$-$C_8$-alkoxy group,

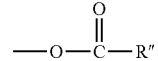

where R" is a linear or branched $C_1$-$C_8$ alkyl group, unsubstituted or substituted -phenyl group, unsubstituted or substituted -naphthyl group, unsubstituted or substituted -vinyl group, -halogen, and halogenated $C_1$-$C_8$-alkyl group;

R₃ is selected from the group consisting of independently selected from the group consisting of —H, —OH, linear or branched $C_1$-$C_8$-alkoxy group, -halogen, and halogenated -alkyl group;

R₄ is selected from the group consisting of independently selected from the group consisting of —H, —OH, linear or branched $C_1$-$C_8$-alkoxy group, -halogen, and halogenated $C_1$-$C_8$-alkyl group;

R₅, identical or different, is independently selected from the group consisting of linear or branched $C_1$-$C_8$ N-alkyl group; hydroxyl-substituted $C_1$-$C_8$ N-alkyl group; fused 5-7 member heterocyclic ring; and unsubstituted or substituted aromatic ring, wherein the substituent on the aromatic ring is selected from the group consisting of linear or branched $C_1$-$C_8$ alkyl group and linear or branched $C_1$-$C_8$ alkoxy group; and R₆, identical or different, is independently selected from the group consisting of linear or branched $C_1$-$C_8$ alkyl group, and unsubstituted or substituted aromatic ring wherein the substituent on the aromatic ring is selected from the group consisting of linear or branched $C_1$-$C_8$ alkyl group, linear or branched $C_1$-$C_8$ alkoxy group, and halogen; and wherein the amine cation constituent is selected from the group consisting of N-methyl morpholine, N-methyl pyrrolidine, N,N-dimethyl aniline, N,N,4-trimethyl aniline, N,N-dimethyl-4-methoxyaniline, N,N-pyrrolidine-4-methoxyaniline, and N,N-ethoxy-4-methylaniline.

8. The quaternary ammonium salt of claim 1, wherein the borate anion constituent is selected from the group consisting of tetraphenyl borate, tetra-4-methyl-phenyl borate, tetra-4-methoxy-phenyl borate, tetra-4-fluoro-phenyl borate, n-butyl-triphenyl borate, s-butyl-triphenyl borate, t-butyl-triphenyl borate, cyclohexyl-triphenyl borate, di-n-butyl-diphenyl borate, tri-n-butyl-phenyl borate, and tetra-n-butyl borate.

9. The quaternary ammonium salt of claim 1, wherein the 3-ketocoumarin constituent is selected from the group consisting of dimethoxy-ketocoumarin, di-n-butoxy-ketocoumarin, difluoro-ketocoumarin, diphenyl-ketocoumarin, divinyl-ketocoumarin, trimethoxy-ketocoumarin, tetramethoxy-ketocoumarin, 3,4-benzo-ketocoumarin, and 4,5-benzo-ketocoumarin.

10. A photobase-redox initiating system comprising a quaternary ammonium salt and a peroxide,
wherein the quaternary ammonium salt comprises a chromophore constituent, a tertiary amine cation constituent connected to the para-position of the chromophore constituent via a methylene linkage, and a borate anion constituent, wherein chromophore constituent is a 3-ketocoumarin constituent and the quaternary ammonium salt has the formula (I) or the chromophore constituent is a benzophenone constituent and the quaternary ammonium salt has the formula (II)

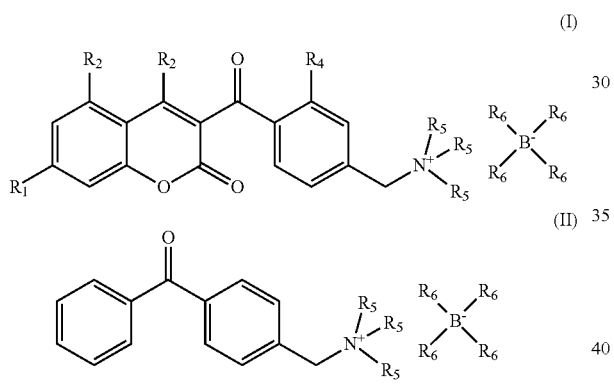

wherein
R$_1$ and R$_2$, identical or different, are independently selected from the group consisting of —H, —OH, linear or branched C$_1$-C$_8$-alkoxy group,

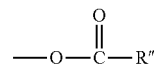

where R″ is a linear or branched C$_1$-C$_8$ alkyl group, unsubstituted or substituted -phenyl group, unsubstituted or substituted -naphthyl group, unsubstituted or substituted -vinyl group, -halogen, and halogenated C$_1$-C$_8$-alkyl group;

R$_3$ is selected from the group consisting of independently selected from the group consisting of —H, —OH, linear or branched C$_1$-C$_8$-alkoxy group, -halogen, and halogenated -alkyl group;

R$_4$ is selected from the group consisting of independently selected from the group consisting of —H, —OH, linear or branched C$_1$-C$_8$-alkoxy group, -halogen, and halogenated C$_1$-C$_8$-alkyl group;

R$_5$, identical or different, is independently selected from the group consisting of linear or branched C$_1$-C$_8$ N-alkyl group; hydroxyl-substituted C$_1$-C$_8$ N-alkyl group; fused 5-7 member heterocyclic ring; and unsubstituted or substituted aromatic ring, wherein the substituent on the aromatic ring is selected from the group consisting of linear or branched C$_1$-C$_8$ alkyl group and linear or branched C$_1$-C$_8$ alkoxy group; and R$_6$, identical or different, is independently selected from the group consisting of linear or branched C$_1$-C$_8$ alkyl group, and unsubstituted or substituted aromatic ring wherein the substituent on the aromatic ring is selected from the group consisting of linear or branched C$_1$-C$_8$ alkyl group, linear or branched C$_1$-C$_8$ alkoxy group, and halogen; and wherein the peroxide is selected from the group consisting of benzoyl peroxide, dilauroyl peroxide, dialkylperoxydicarbonate, phthaloyl peroxide, dicumyl peroxide, and combinations thereof.

11. The quaternary ammonium salt of claim 1, wherein the amine cation constituent is selected from the group consisting of N-methyl morpholine, N-methyl pyrrolidine, N,N-dimethyl aniline, N,N,4-trimethyl aniline, N,N-dimethyl-4-methoxyaniline, N,N-pyrrolidine-4-methoxyaniline, and N,N-ethoxy-4-methylaniline.

* * * * *